(12) United States Patent
Vauzeilles et al.

(10) Patent No.: US 10,717,718 B2
(45) Date of Patent: Jul. 21, 2020

(54) 5-AZIDO-5-DEOXY-2:3-ISOPROPYLIDENE-D-ARABINOSE COMPOUNDS; THEIR METHOD OF MANUFACTURE AND THEIR USE FOR THE SYNTHESIS OF ARA-N3, KDO-N3 AND 4EKDO-N3

(71) Applicant: Centre National de la Recherche Scientifique, Paris (FR)

(72) Inventors: Boris Vauzeilles, Sceaux (FR); Jordi Mas Pons, Barcelone (ES); Aurèlie Baron, L'Isle Adam (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/777,060

(22) PCT Filed: Nov. 16, 2016

(86) PCT No.: PCT/EP2016/077900
§ 371 (c)(1),
(2) Date: May 17, 2018

(87) PCT Pub. No.: WO2017/085144
PCT Pub. Date: May 26, 2017

(65) Prior Publication Data
US 2018/0370942 A1 Dec. 27, 2018

(30) Foreign Application Priority Data
Nov. 17, 2015 (EP) .................. 15306824

(51) Int. Cl.
| C07D 317/30 | (2006.01) |
| C07H 5/04 | (2006.01) |
| C07H 7/027 | (2006.01) |
| C07D 317/28 | (2006.01) |
| C07H 13/00 | (2006.01) |
| C07H 9/04 | (2006.01) |
| C07H 1/00 | (2006.01) |
| G01N 33/569 | (2006.01) |

(52) U.S. Cl.
CPC ......... *C07D 317/30* (2013.01); *C07D 317/28* (2013.01); *C07H 1/00* (2013.01); *C07H 5/04* (2013.01); *C07H 7/027* (2013.01); *C07H 9/04* (2013.01); *C07H 13/00* (2013.01); *G01N 33/56911* (2013.01)

(58) Field of Classification Search
CPC ............... C07D 317/30; C07D 317/28; G01N 33/56911; C07H 7/027; C07H 5/04
USPC .......................................................... 536/55
See application file for complete search history.

(56) References Cited

FOREIGN PATENT DOCUMENTS

WO WO 2013/107759 7/2013

OTHER PUBLICATIONS

International Search Report, PCTEP2016/077900, dated Jan. 25, 2017.
Renee Whizar et al: "A Simple Synthesis of C-8 Modified 2-Keto-3-deoxy-d-manno-octulosonic Acid (KDO) Derivatives", Synlett, vol. 2010, No. 04, Feb. 2, 2010 (Feb. 2, 2010), pp. 583-586, XP055248908, DE ISSN: 0936-5214, DOI: 10.1055/s-0029-1219356.

*Primary Examiner* — Shaojia A Jiang
*Assistant Examiner* — Michael C Henry
(74) *Attorney, Agent, or Firm* — Young & Thompson

(57) ABSTRACT

Disclosed are new compounds of formulae:

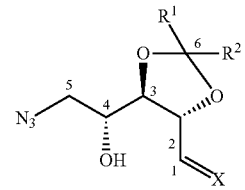

Formula V, X = NOR$^3$;
Formula VI, X = O

Wherein: $R^1$ and $R^2$ can be independently H; a $C_1$ to $C_6$ alkyl including methyl, ethyl, propyl, butyl; aryl including phenyl, para-methoxyphenyl; or $R^1$,$R^2$ together with the carbon C-6 can be a cyclopentylidene or cyclohexylidene; each of these groups being substituted or not; and $R^3$ can be a $C_1$ to $C_6$ alkyl including methyl, ethyl, propyl, isopropyl, butyl, isobutyl, tert-butyl, pentyl; or aryl including phenyl, methylphenyl, ethylphenyl, each of these groups being substituted or not. The invention also relates to their method of manufacture and their use for the synthesis of Ara-$N_3$, Kdo-$N_3$ and 4eKdo-$N_3$.

15 Claims, No Drawings

US 10,717,718 B2

5-AZIDO-5-DEOXY-2:3-ISOPROPYLIDENE-D-ARABINOSE COMPOUNDS; THEIR METHOD OF MANUFACTURE AND THEIR USE FOR THE SYNTHESIS OF ARA-N3, KDO-N3 AND 4EKDO-N3

INTRODUCTION

The invention relates to a new synthesis intermediate compound 5-azido-5-deoxy-2:3-isopropylidene D-arabinose, which is a key compound towards the synthesis of either known Kdo-$N_3$, or known 4eKdo-$N_3$ or even known Ara-$N_3$, by a new synthesis route with excellent yield and excellent purity and easy purification steps, together with its method of preparation and the use thereof for the synthesis of either known Kdo-$N_3$, or known 4eKdo-$N_3$ or even known Ara-$N_3$. According to a best particular mode, the synthesis starts from the commercially available D-arabinose and is providing an overall yield of 17 mol % for Kdo-$N_3$ with a purity of more than 95%, an overall yield of 6 mol % for 4eKdo-$N_3$ with a purity of more than 95% and an overall yield of 26 mol % for Ara-$N_3$ with a purity of more than 95%.

The invention further relates to synthesis intermediates, which are claimed as new compounds, selected from the group consisting of compounds of formulae IV, V, VI, VIIIa, VIIIb, IXa and IXb. More precisely, the invention further relates to specific synthesis intermediates selected from the group consisting of compounds (4), (5), (6), (8a), (9a), (8b) and (9b), set forth here-below.

More particularly, all these compounds, including a compound of formula V or VI and in particular of formula (5) or (6), or a compound of formula VIIIa or VIIIb, and in particular of formula (8a) or (8b), or a compound of formula IXa or IXb, and in particular of formula (9a) or (9b), could be used for metabolic labeling of Gram negative and Gram positive bacteria or other organisms.

Especially, these compounds could be used for detecting viable bacteria in labeling the bacterial enveloppe thereof via metabolic modification of enveloppe glycans thereof, especially the LipoPolySaccharides or LPS layer in case of Gram negative bacteria, by incorporating into their enveloppe glycans, especially their LPS, a modified component bearing a bio orthogonal chemical reporter, thus decorating the cell surface and enabling the detection thereof with a chemistry reaction, especially click chemistry reaction, allowing further detecting of the chemical reporter, in an overall rapid process. This detection with a chemical reaction, especially click chemistry is well known to one skilled in the art as reported below. These bacteria can be, without limitation, selected from the following genus of bacteria: *Acinetobacter, Bacteroides, Bartonella, Bordetella, Brachyspira, Brucella, Burkholderia, Campylobacter, Cardiobacterium, Chlamydophila, Chryseobacterium, Clostridium, Coxiella, Cronobacter, Edwardsiella, Ehrlichia, Eikenella, Elizabethkingia, Enterobacter, Escherichia, Francisella, Fusobacterium, Haemophilus, Helicobacter, Klebsiella, Legionella, Leptospira, Morganella, Myxococcus, Neisseria, Neorickettsia, Pasteurella, Plesiomonas, Porphyromonas, Prevotella, Proteus, Providencia, Pseudoalteromonas, Pseudomonas, Rickettsia, Rhodocycclus, Salmonella, Serratia, Sinorhizobium, Shigella, Schewanella, Shewamma, Stenotrophomonas, Streptobacillus, Tenacibaculum, Treponema, Vibrio, Yersinia.*

DISCUSSION OF PRIOR ART

Dumont et al in WO 2013/107759, and *Angew. Chem. Int. Ed.*, 2012, 51, P 3143-3146, and *Angew. Chem.*, 2012, 124, P3197-3200 have previously shown that metabolic glycan labelling, in which a modified monosaccharide bearing a reporter function is metabolically incorporated into surface glycans, could be efficiently used to target bacterial LPS (LipoPolySaccharides) without species specificity. In this first study, an azido derivative of 3-deoxy-D-manno-octulosonic acid, or KetoDeoxyOctonic acid, also named Kdo, a bacterial monosaccharide, was incorporated into the LPS inner core of various Gram-negative bacteria, thereby allowing to detect the bacteria by a so-called click chemistry. This azido derivative was 8-azido-8-deoxy-Kdo, compound 1 in Scheme 2 of Dumont et al., 2012, 51, P 3144.

With regard to the chemical synthesis of this 8-azido-8-deoxy-Kdo, Dumont et al performs a condensation of 5-azido-5-deoxy-D-arabinofuranose or Ara-$N_3$ with sodium oxaloacetate, the product being isolated as its ammonium salt in 57% yield (86% based on recovered Ara-$N_3$) after decarboxylation under slightly acidic conditions, see Dumont et al., 2012, 51 Scheme 3 and the second full paragraph, P 3144.

Further, Dumont article mentions that Ara-$N_3$ can be obtained by a very direct, simple, and time-saving strategy from commercial D-arabinose. More information is accessible on a supporting information available on internet at http://dx.doi.org/10.1002/anie.201108127.

But Dumont et al in WO 2013/107759, discloses from page 28, line 16 the full synthesis. Ara-$N_3$ is prepared from commercial D-arabinose by a step of tosylation of the primary alcohol of D-arabinofuranose which is then acetylated to protect the remaining alcohols, and then reacted with sodium azide (NaN$_3$), plus deacetylation with an overall yield of 15 mol %. It is said that the product 6, Ara-$N_3$, could be easily purified by flash chromatography. See page 29, and scheme 1 of WO 2013/107759.

The synthesis of 5-azido-5-deoxy-D-arabinofuranose and of ammonium 8-azido-3,8-dideoxy-D-manno-octulosonate is then described on pages 29-31, Ex 1c (see scheme 2 on page 31).

The drawback of this synthesis lies in a poor yield of not more than about 15 mol % to obtain Ara-$N_3$ and also to obtain Kdo-$N_3$ and a greater difficulty to purify the Kdo-$N_3$ obtained from the reaction medium. Indeed, the Kdo-$N_3$ is obtained in a low purification yield and a low reproducibility prohibiting to think about an industrial implementation.

The article by GILLINGHAM et al. in *Nature Chemistry*, vol. 2, NR 2, 2010, P 102-105 and in its supplementary information (2010) available on internet at www.nature.com/naturechemistry, pages 1-34 discloses the synthesis of 2:3,4:5-diisopropylidene-D-arabinose O-methyloxime (23) from D-arabinose, by reacting with methoxyamine HCl, on page 6, herein-after named compound (2) of Formula II; and the synthesis of 2:3-isopropylidene-D-arabinose O-methyloxime (26) from (23), in AcOH under reduced pressure, on page 7 herein-after named compound (3) of Formula III.

Problems to be Solved by the Invention

A main aim of the present invention lies in solving the technical problem of finding a new synthesis route with excellent yield, excellent purity and easy purification steps towards the synthesis of either known Kdo-$N_3$, or known 4eKdo-$N_3$ or even known Ara-$N_3$.

Another main aim of the present invention lies in solving this technical problem according to a technical solution which is believed to be extrapolatable, reliably and reproducibly at the industrial scale.

A further aim of the invention is to prepare the known Kdo-N₃, or known 4eKdo-N₃ or even known Ara-N₃ through this new synthesis route, from commercially available D-arabinose.

The invention method solves this technical problem by providing a new synthesis route which reaches the known Kdo-N₃, or known 4eKdo-N₃ or even known Ara-N₃ with excellent yield, excellent purity and easy purification steps, notably with use of flash chromatography.

The invention method used for synthesis of Kdo-N₃ and 4eKdo-N₃ further relies on an indium-promoted coupling step which maintains the integrity of an azido group. This central elongation step was not obvious since indium is known to efficiently reduce azido groups into amino groups.

The invention method permits to avoid the use of ion exchange resin column chromatographies for the separation of Kdo-N₃ and 4eKdo-N₃. This purification method gives low and poorly reproducible isolated yields and purity for Kdo-N₃ and sometimes leads to the formation of non-separable impurities. Moreover, 4eKdo-N₃ was very difficult to isolate in pure form.

The invention method allows avoiding last step condensation with sodium oxaloacetate which conditions are difficult to precisely control and involves a strict control of pH and sometimes leads to the formation of impurities that are very difficult to eliminate, making the invention method more easily reproducible.

A further aim of the invention is to provide new synthesis intermediate compounds.

Another further aim of the invention is to use at least some of these new synthesis intermediate compounds for the detection of bacteria, in particular Gram negative or Gram positive bacteria, including without limitation, the following genus of bacteria: *Acinetobacter, Bacteroides, Bartonella, Bordetella, Brachyspira, Bruce/la, Burkholderia, Campylobacter, Cardiobacterium, Chlamydophila, Chryseobacterium, Clostridium, Coxiella, Cronobacter, Edwardsiella, Ehrlichia, Eikenella, Elizabethkingia, Enterobacter, Escherichia, Francisella, Fusobacterium, Haemophilus, Helicobacter, Klebsiella, Legionella, Leptospira, Morganella, Myxococcus, Neisseria, Neorickettsia, Pasteurella, Plesiomonas, Porphyromonas, Prevotella, Proteus, Providencia, Pseudoalteromonas, Pseudomonas, Rickettsia, Rhodocycclus, Salmonella, Serratia, Sinorhizobium, Shigella, Schewanella, Shewamma, Stenotrophomonas, Streptobacillus, Tenacibaculum, Treponema, Vibrio, Yersinia.*

SUMMARY OF THE INVENTION

The above technical problems are solved by the invention as defined by the claims.

In the description and claims, the abbreviations have their usual meaning known to one skilled in the chemical art. For instance:
Me is for Methyl; Et is for Ethyl; Ms is for Methanesulfonyl;
Kdo is for 3-deoxy-D-manno-octulosonic acid, or KetoDeoxyOctonic acid;
Kdo-N₃ is for 8-azido-3,8-dideoxy-D-manno-oct-2-ulosonate and 4eKdo-N₃ for its diastereoiomer in the 4 position, named 8-azido-3,8-dideoxy-D-gluco-oct-2-ulosonate;
Ara-N₃ is for 5-azido-5-deoxy-D-arabinofuranose.

According to a first aspect, the invention relates to a new synthesis intermediate compound, which is claimed as a new compound, of formula V or VI, selected from:

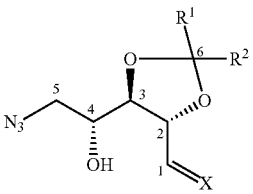

Formula V, X = NOR³;
Formula VI, X = O

Wherein:
R¹ and R² can be independently H; a C₁ to C₆ alkyl including methyl, ethyl, propyl, butyl; aryl including phenyl, para-methoxyphenyl; or R¹,R² together with the carbon C-6 can be a cyclopentylidene or cyclohexylidene; each of these groups being substituted or not;
and R³ can be a C₁ to C₆ alkyl including methyl, ethyl, propyl, isopropyl, butyl, isobutyl, tert-butyl, pentyl; or aryl including phenyl, methylphenyl, ethylphenyl, each of these groups being substituted or not.

According to a particular embodiment, the invention relates to a new synthesis intermediate compound, which is claimed as a new compound, of formula V:

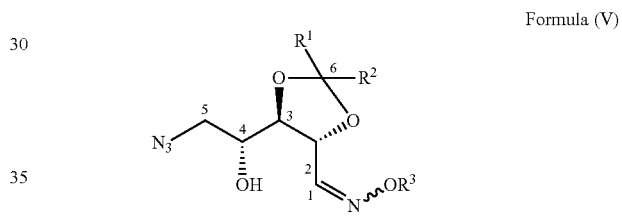

Formula (V)

Wherein:
R¹ and R² can be independently H; a C₁ to C₆ alkyl including methyl, ethyl, propyl, butyl; aryl including phenyl, para-methoxyphenyl; or R¹,R² together with the carbon C-6 can be a cyclopentylidene or cyclohexylidene; each of these groups being substituted or not.
and R³ can be a C₁ to C₆ alkyl including methyl, ethyl, propyl, isopropyl, butyl, isobutyl, tert-butyl, pentyl; or aryl including phenyl, methylphenyl, ethylphenyl, each of these groups being substituted or not.

More particularly, the invention relates to the specific synthesis intermediate compound (5), which is claimed as new compound, named 5-Azido-5-deoxy-2:3-isopropylidene-D-arabinose O-methyloxime (5):

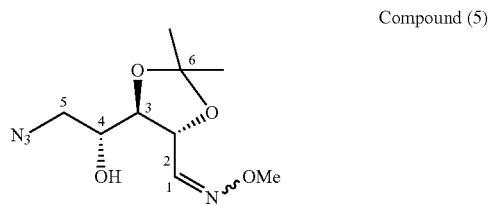 [SMILES: CON=C[C@H]1OC(C)(C)O[C@@H]1[C@H](O)CN=[N+]=[N-]]

Compound (5)

According to another particular embodiment, the invention relates to a new synthesis intermediate compound, which is claimed as a new compound, of formula VI:

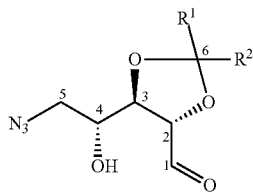

Formula (VI)

Wherein:
$R^1$ and $R^2$ can be independently H; a $C_1$ to $C_6$ alkyl including methyl, ethyl, propyl, butyl; aryl including phenyl, para-methoxyphenyl; or $R^1,R^2$ together with the carbon C-6 can be a cyclopentylidene or cyclohexylidene; each of these groups being substituted or not.

More particularly, the invention relates to the specific synthesis intermediate compound (6), which is claimed as new compound, named 5-Azido-5-deoxy-2:3-isopropylidene-D-arabinose (6):

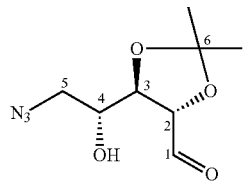

Compound (6)

According to a second aspect, the invention provides a method of preparation of synthesis intermediate compound of formula VI, comprising the chemical reaction of the compound of formula V:

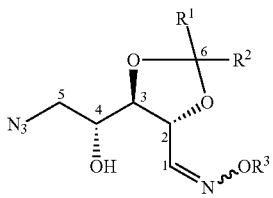

Formula (V)

Wherein:
$R^1$ and $R^2$ can be independently H; a $C_1$ to $C_6$ alkyl including methyl, ethyl, propyl, butyl; aryl including phenyl, para-methoxyphenyl; or $R^1,R^2$ together with the carbon C-6 can be a cyclopentylidene or cyclohexylidene; each of these groups being substituted or not;
and $R^3$ can be a $C_1$ to $C_6$ alkyl including methyl, ethyl, propyl, isopropyl, butyl, isobutyl, tert-butyl, pentyl; or aryl including phenyl, methylphenyl, ethylphenyl, each of these groups being substituted or not;
with an aqueous solution of an organic or inorganic acid in the presence of an aldehyde.

According to a particular feature, compound of formula VI could be obtained by reaction of compound of formula V (10 mg to 100 g), with an aqueous solution of an organic or inorganic acid (0.01 to 0.50 M of compound of formula V), such as acetic acid, p-toluenesulfonic acid, hydrochloric acid, typically an aqueous solution of acetic acid (60 to 90%, v/v) and the presence of an aldehyde (0.5 to 50.0 equivalents), typically formaldehyde, at a temperature between 0 and 100° C.

More particularly, the invention provides a method of preparation of specific synthesis intermediate compound (6), comprising the chemical reaction of compound (5), named 5-azido-5-deoxy-2:3-isopropylidene-D-arabinose O-methyloxime:

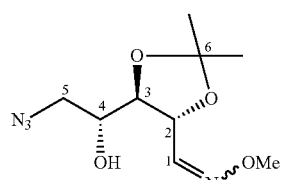

Compound (5)

under the above same reaction conditions as the preparation of compound VI.

According to a particular embodiment, the invention relates to the preparation of synthesis intermediate compound of formula V, comprising the chemical reaction of a compound of formula IV:

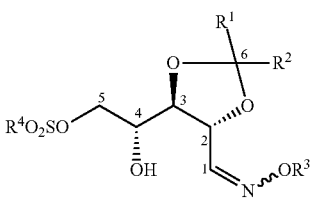

Formula (IV)

Wherein:
$R^1$ and $R^2$ can be independently H; a $C_1$ to $C_6$ alkyl including methyl, ethyl, propyl, butyl; aryl including phenyl, para-methoxyphenyl; or $R^1,R^2$ together with the carbon C-6 can be a cyclopentylidene or cyclohexylidene; each of these groups being substituted or not;
and $R^3$ can be a $C_1$ to $C_6$ alkyl including methyl, ethyl, propyl, isopropyl, butyl, isobutyl, tert-butyl, pentyl; or aryl including phenyl, methylphenyl, ethylphenyl, each of these groups being substituted or not;
and $R^4$ can be a $C_1$ to $C_6$ alkyl including methyl, ethyl, propyl; a $C_1$ to $C_6$ perfluoroalkyl including trifluoromethyl, pentafluoroethyl; or aryl including para-methylphenyl, para-nitrophenyl; each of these groups being substituted or not; with an organic or inorganic azide salt in non-polar solvent or in a polar aprotic solvent.

According to a particular feature, compound of formula V could be obtained by reaction of compound of formula IV (10 mg to 100 g), with an organic or inorganic azide salt (0.8 to 15.0 equivalents) such as sodium azide, lithium azide, tetrabutylammonium azide, preferably sodium azide, in a non-polar solvent such as pentane, hexane, cyclohexane, benzene, toluene, chloroform, diethyl ether, dioxane, or in a polar aprotic solvent (0.01 to 0.50 M), such as chloroform, dichloromethane, tetrahydrofuran, ethyl acetate, acetone, N,N-dimethylformamide, acetonitrile, dimethylsulfoxide, typically N,N-dimethylformamide, at a temperature between 0 and 150° C.

More particularly, the invention relates to the preparation of specific synthesis intermediate compound (5), comprising the chemical reaction of compound (4), named 2:3-isopropylidene-5-O-methanesulfonyl-D-arabinose O-methyloxime:

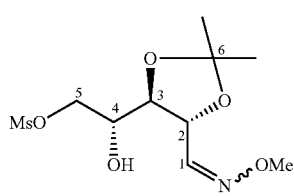

Compound (4)

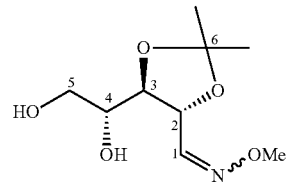

Compound (3)

under the above same reaction conditions as the preparation of compound V.

According to another particular embodiment, the invention relates to the preparation of synthesis intermediate compound of formula IV, comprising the chemical reaction of compound of formula III:

under the above same reaction conditions as the preparation of compound IV.

According to another particular embodiment, the invention relates to the preparation of synthesis intermediate compound of formula III, comprising the chemical reaction of a compound of formula II:

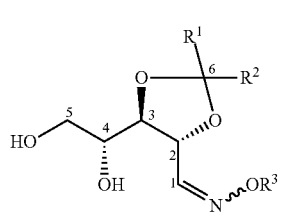

Formula (III)

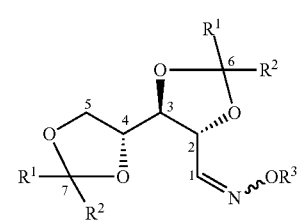

Formula (II)

Wherein:

$R^1$ and $R^2$ can be independently H; a $C_1$ to $C_6$ alkyl including methyl, ethyl, propyl, butyl; aryl including phenyl, paramethoxyphenyl; or $R^1, R^2$ together with the carbon C-6 can be a cyclopentylidene or cyclohexylidene; each of these groups being substituted or not;

and $R^3$ can be a $C_1$ to $C_6$ alkyl including methyl, ethyl, propyl, isopropyl, butyl, isobutyl, tert-butyl, pentyl; or aryl including phenyl, methylphenyl, ethylphenyl, each of these groups being substituted or not;

with a sulfonyl chloride or sulfonic anhydride in the presence of an organic base and in the presence or not of a polar aprotic solvent.

According to a particular feature, compound of formula IV could be obtained by reaction of compound of formula III (10 mg to 100 g), with a sulfonyl chloride or sulfonic anhydride (0.8 to 4.0 equivalents), such as methanesulfonyl chloride, p-toluenesulfonyl chloride, p-nitrobenzenesulfonyl chloride, methanesulfonic anhydride, trifluoromethanesulfonic anhydride, preferably methanesulfonyl chloride, in the presence of an organic base (0.8 to 200 equivalents), such as pyridine, triethylamine, diisopropylethylamine and in the presence or not of a polar aprotic solvent (0.05 to 0.50 M), such as chloroform, dichloromethane, tetrahydrofuran, ethyl acetate, acetone, N,N-dimethylformamide, acetonitrile, dimethylsulfoxide, at a temperature between −30 and 100° C.

More particularly, the invention relates to the preparation of specific synthesis intermediate compound (4), comprising the chemical reaction of compound (3), named 2:3-isopropylidene-D-arabinose O-methyloxime, known per se from GILLINGHAM cited above:

Wherein:

$R^1$ and $R^2$ can be independently H; a $C_1$ to $C_6$ alkyl including methyl, ethyl, propyl, butyl; aryl including phenyl, paramethoxyphenyl; or $R^1, R^2$ together with the carbon C-6 can be a cyclopentylidene or cyclohexylidene; each of these groups being substituted or not;

and $R^3$ can be a $C_1$ to $C_6$ alkyl including methyl, ethyl, propyl, isopropyl, butyl, isobutyl, tert-butyl, pentyl; or aryl including phenyl, methylphenyl, ethylphenyl, each of these groups being substituted or not;

by deprotection of terminal diol with an aqueous solution of an organic or inorganic acid.

According to a particular feature, compound of formula III could be obtained from compound of formula II (10 mg to 100 g) by deprotection of terminal diol with an aqueous solution of an organic or inorganic acid (0.01 to 0.50 M of compound of formula II), such as formic acid, acetic acid, trifluoroacetic acid, p-toluenesulfonic acid, sulphuric acid, hydrochloric acid, typically an aqueous solution of acetic acid (60 to 90%, v/v), at reduced pressure (150 to 400 mbar) and at temperature between 20 and 60° C.

More particularly, the invention relates to the preparation of specific synthesis intermediate compound (3), comprising the chemical reaction of compound (2), named 2:3,4:5-di isopropylidene-D-arabinose O-methyloxime known per se from GILLINGHAM cited above:

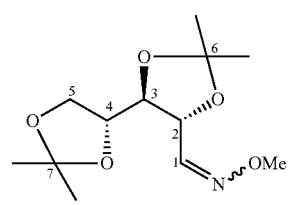

Compound (2)

under the above same reaction conditions as the preparation of compound III.

According to a further particular embodiment, the invention relates to preparation of synthesis intermediate of formula II, comprising the chemical reaction of D-arabinose with an O-alkylhydroxylamine hydrochloride, an O-phenylhydroxylamine hydrochloride, substituted or not in its aromatic ring or O-benzylhydroxylamine hydrochloride substituted or not in its aromatic ring in the presence of an organic base, with or without a protic solvent; the crude residue being then reacted with a ketone, an aldehyde or the corresponding ketal, in the presence of a Brönsted or Lewis acid.

According to a particular feature, compound of formula II could be obtained by reaction of D-arabinose (10 mg to 100 g) and an O-alkylhydroxylamine hydrochloride, an O-phenylhydroxylamine hydrochloride, substituted or not in its aromatic ring or O-benzylhydroxylamine hydrochloride substituted or not in its aromatic ring (0.5 to 15.0 equivalents), such as O-methylhydroxylamine, O-ethylhydroxylamine, O-propylhydroxylamine, O-isopropylhydroxylamine, O-(1-methyl propyl)hydroxylamine, O-butylhydroxylamine, O-isobutylhydroxylamine, O-tert-butylhydroxylamine, O-pentylhydroxylamine, O-methyl butylhydroxyamine, O-(1,2-dimethylpropyl)hydroxylamine, O-(2,2-dimethyl propyl)hydroxylamine; or such as O-phenylhydroxylamine, O-(2-methyl phenyl)hydroxylamine, O-(3-methylphenyl)hydroxylamine, O-(4-methyl phenyl)hydroxylamine, O-(4-ethylphenyl)hydroxylamine; typically O-methylhydroxylamine, in the presence of an organic base (0.8 to 100 equivalents), such as pyridine, triethylamine, diisopropylethylamine, typically pyridine, with or without a protic solvent (0.05 to 0.50 M), such as tert-butanol, n-propanol, isopropanol, ethanol, methanol, preferably methanol or ethanol, at a temperature between −10 and 100° C. Then the crude residue could be reacted with a ketone, an aldehyde or the corresponding ketal (1.5 to 50.0 equivalents), such as formaldehyde, acetaldehyde, paraldehyde, 1,1-diethoxyethane, acetone, 2,2-dimethoxypropane, 2-methoxypropene, 2-butanone, cyclohexanone, 1,1 dimethoxycyclohexane, 1-ethoxycyclohexene, typically 2,2-dimethoxypropane, in the presence of a Brönsted or Lewis acid (0.01 to 10.0 equivalents) such as sulphuric acid, p-toluenesulfonic acid, pyridinium p-toluenesulfonate, camphorsulfonic acid, typically p-toluenesulfonic acid, at a temperature between 0 and 100° C.

According to a third aspect, the invention relates to the use of synthesis intermediate compound of formula VI for the synthesis of 5-azido-5-deoxy-D-arabinofuranose or Ara-N$_3$ (7):

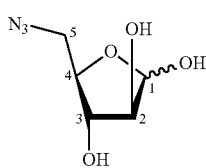

Compound (7)

comprising reacting synthesis intermediate compound of formula VI, under reaction conditions providing removal of protecting group of compound of formula VI with an aqueous solution of an organic or inorganic acid in a polar aprotic solvent or non-polar solvent.

According to a particular feature, the product of interest 7 could be prepared by removal of protecting group of compound of formula VI (10 mg to 100 g) with an aqueous or alcoholic solution (30 to 70%, v/v) of an organic or inorganic acid (10 to 200 equivalents), such as formic acid, acetic acid, trifluoroacetic acid, p-toluenesulfonic acid, sulphuric acid, hydrochloric acid, or an acidic resin (10 to 200 equivalents), such as Amberlyst® 15, Dowex® 50 W, Amberlite® IR, typically trifluoroacetic acid; in a polar aprotic solvent (0.01 to 0.50 M), such as chloroform, dichloromethane, tetrahydrofuran, ethyl acetate, acetone, N,N-dimethylformamide, acetonitrile, dimethylsulfoxide or non-polar solvent such as pentane, hexane, cyclohexane, benzene, toluene, chloroform, diethyl ether, dioxane, typically dichloromethane, or a protic solvent such as an alcohol, at a temperature between 0 and 100° C.

Further, the invention relates to the use of synthesis intermediate compound of formula VI for the synthesis of intermediate of formula VIIIa:

Formula (VIIIa)

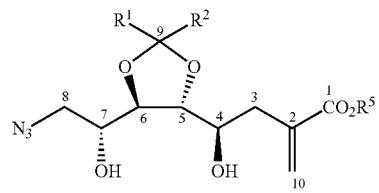

Wherein:

R$^1$ and R$^2$ can be independently H; a C$_1$ to C$_6$ alkyl including methyl, ethyl, propyl, butyl; aryl including phenyl, para-methoxyphenyl; or R$^1$,R$^2$ together with the carbon C-6 can be a cyclopentylidene or cyclohexylidene; each of these groups being substituted or not;

and R$^5$ can be a C$_1$ to C$_6$ alkyl including methyl, ethyl, propyl, butyl, t-butyl, pentyl, hexyl; or benzyl; each of these groups being substituted or not;

by reaction of compound of formula VI with alkyl 2-(halomethyl)acrylate, in the presence of a metal such as indium, and the presence or not of an aqueous solution of an organic or inorganic acid, in a protic solvent or in a mixture of water and a polar aprotic solvent.

According to a particular feature, compound of formula VIIIa could be obtained by reaction of compound of formula VI (10 mg to 50 g) with alkyl 2-(halomethyl)acrylate (1.0 to 15.0 equivalents), in the presence of indium (0.8 to 3.0 equivalents), and in the presence or not of an aqueous solution of an organic or inorganic acid (0.5 to 10.0 equivalents), such as formic acid, hydrochloric acid, preferably formic acid (5 to 20%, v/v), in a protic solvent such as tert-butanol, n-propanol, isopropanol, ethanol, methanol, preferably ethanol or a mixture of water and a polar aprotic solvent such as chloroform, dichloromethane, tetrahydrofuran, ethyl acetate, acetone, N,N-dimethylformamide, acetonitrile, dimethylsulfoxide (0.01 to 0.30 M), typically acetonitrile, at a temperature between −20 and 60° C.

More particularly, the invention relates to the use of specific synthesis intermediate compound (6) for the synthesis of compound (8a), named ethyl (4R)-4-{(4R,5R)-5-[(R)-2-azido-1-hydroxyethyl]-2,2-dimethyl-1,3-dioxolan-4-yl)-4-hydroxy-2-methylenebutanoate:

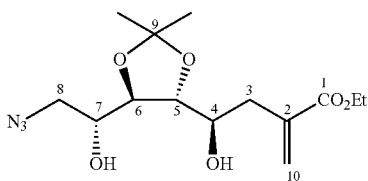

Compound (8a)

under the above same reaction conditions as the preparation of compound VIIIa.

The invention further relates to the use of the compound of formula VIIIa for the preparation of intermediate of formula IXa:

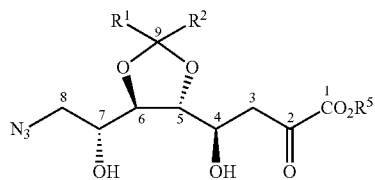

Formula (IXa)

Wherein:
$R^1$ and $R^2$ can be independently H; a $C_1$ to $C_6$ alkyl including methyl, ethyl, propyl, butyl; aryl including phenyl, para-methoxyphenyl; or $R^1, R^2$ together with the carbon C-6 can be a cyclopentylidene or cyclohexylidene; each of these groups being substituted or not;
and $R^5$ can be a $C_1$ to $C_6$ alkyl including methyl, ethyl, propyl, butyl, t-butyl, pentyl, hexyl; or benzyl; each of these groups being substituted or not;
comprising performing an ozonolysis of compound of formula VIIIa with ozone in a protic solvent, at a temperature between −100 and 0° C., and then the unstable intermediate compound being reacted with a reducing agent, in a protic solvent.

According to a particular feature, compound of formula IXa could be obtained by ozonolysis of compound of formula VIIIa (10 mg to 50 g) with ozone in a protic solvent (0.01 to 0.10 M), such as tert-butanol, n-propanol, isopropanol, ethanol, methanol, typically methanol, at a temperature between −100 and 0° C. Then the unstable intermediate compound could be reacted with a reducing agent (0.8 to 50.0 equivalents) such as triphenylphosphine, thiourea or dimethyl sulfide, typically dimethyl sulfide, in a protic solvent (0.01 to 0.10 M), such as tert-butanol, n-propanol, isopropanol, ethanol, methanol, typically methanol, at a temperature between −20 and 40° C.

More particularly, the invention relates to the use of specific compound (8a) for the preparation of specific compound (9a), named (4R)-4-{(4R,5R)-5-[(R)-2-azido-1-hydroxyethyl]-2,2-dimethyl-1,3-dioxolan-4-yl}-4-hydroxy-2-oxobutanoate:

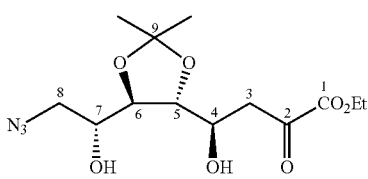

Compound (9a)

under the above same reaction conditions as the preparation of compound IXa.

The invention further relates to the use of the compound of formula IXa for the preparation of ammonium 8-azido-3,8-dideoxy-D-manno-oct-2-ulosonate or Kdo-$N_3$ (10a):

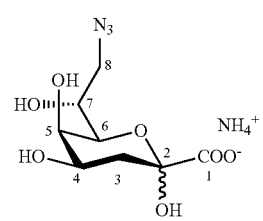

Compound (10a)

comprising deprotecting compound of formula IXa with an aqueous solution of an organic or inorganic acid.

According to a particular feature, the product of interest (10a) could be obtained by deprotection of compound of formula IXa (10 mg to 50 g) with an aqueous solution of an organic or inorganic acid (20 to 200 equivalents), such as acetic acid, trifluoroacetic acid, sulphuric acid, hydrochloric acid, preferably trifluoroacetic acid (5 to 30%, v/v), at a temperature between 0 and 80° C.

According to another embodiment, the invention relates to the use of synthesis intermediate compound of formula VI for the synthesis of intermediate of formula VIIIb:

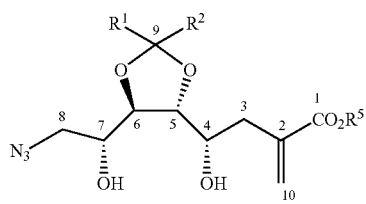

Formula (VIIIb)

Wherein:
$R^1$ and $R^2$ can be independently H; a $C_1$ to $C_6$ alkyl including methyl, ethyl, propyl, butyl; aryl including phenyl, para-methoxyphenyl; or $R^1, R^2$ together with the carbon C-6 can be a cyclopentylidene or cyclohexylidene; each of these groups being substituted or not;
and $R^5$ can be a $C_1$ to $C_6$ alkyl including methyl, ethyl, propyl, butyl, t-butyl, pentyl, hexyl; or benzyl; each of these groups being substituted or not;
by reaction of compound of formula VI with alkyl 2-(halomethyl)acrylate, in the presence of a metal such as indium, and the presence or not of an aqueous solution of an organic or inorganic acid, in a protic solvent or in a mixture of water and a polar aprotic solvent.

According to a particular feature, compound of formula VIIIb could be obtained by reaction of compound of formula VI (10 mg to 50 g) with alkyl 2-(halomethyl)acrylate (1.0 to 15.0 equivalents), in the presence of indium (0.8 to 3.0 equivalents), and in the presence or not of an aqueous solution of an organic or inorganic acid (0.5 to 10.0 equivalents), such as formic acid, hydrochloric acid, preferably formic acid (5 to 20%, v/v), in a protic solvent such as tert-butanol, n-propanol, isopropanol, ethanol, methanol, preferably ethanol or a mixture of water and a polar aprotic solvent such as chloroform, dichloromethane, tetrahydrofuran, ethyl acetate, acetone, N,N-dimethylformamide, acetonitrile, dimethylsulfoxide (0.01 to 0.30 M), typically acetonitrile, at a temperature between −20 and 60° C.

More particularly, the invention relates to the use of specific synthesis intermediate compound (6) for the synthesis of specific compound (8b), named ethyl (4S)-4-{(4R,5R)-5-[(R)-2-azido-1-hydroxyethyl]-2,2-dimethyl-1,3-dioxolan-4-yl)-4-hydroxy-2-methylenebutanoate:

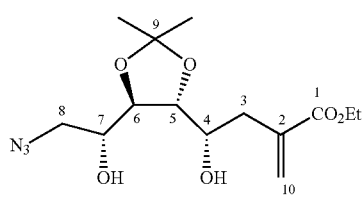

Compound (8b)

under the above same reaction conditions as the preparation of compound VIIIb.

The invention further relates to the use of the compound of formula VIIIb for the preparation of intermediate compound of formula IXb:

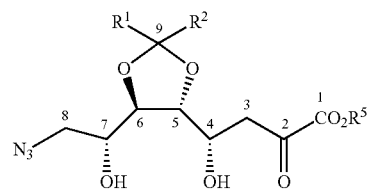

Formula (IXb)

Wherein:
$R^1$ and $R^2$ can be independently H; a $C_1$ to $C_6$ alkyl including methyl, ethyl, propyl, butyl; aryl including phenyl, paramethoxyphenyl; or $R^1$,$R^2$ together with the carbon C-6 can be a cyclopentylidene or cyclohexylidene; each of these groups being substituted or not;
and $R^5$ can be a $C_1$ to $C_6$ alkyl including methyl, ethyl, propyl, butyl, t-butyl, pentyl, hexyl; or benzyl; each of these groups being substituted or not;
comprising performing an ozonolysis of compound of formula VIIIb with ozone in a protic solvent, at a temperature between −100 and 0° C., and then the unstable intermediate compound being reacted with a reducing agent, in a protic solvent.

According to a particular feature, compound of formula IXb could be obtained by ozonolysis of compound of formula VIIIb (10 mg to 50 g) with ozone in a protic solvent (0.01 to 0.10 M), such as tert-butanol, n-propanol, isopropanol, ethanol, methanol, typically methanol, at a temperature between −100 and 0° C. Then the unstable intermediate compound could be reacted with a reducing agent (0.8 to 50.0 equivalents) such as triphenylphosphine, thiourea or dimethyl sulfide, typically dimethyl sulfide, in a protic solvent (0.01 to 0.10 M), such as tert-butanol, n-propanol, isopropanol, ethanol, methanol, typically methanol, at a temperature between −20 and 40° C.

More particularly, the invention relates to the use of specific compound (8b) for the preparation of specific compound (9b), named (4S)-4-{(4R,5R)-5-[(R)-2-azido-1-hydroxyethyl]-2,2-dimethyl-1,3-dioxolan-4-yl)-4-hydroxy-2-oxobutanoate:

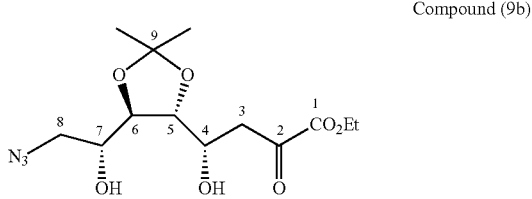 [SMILES: CCOC(=O)C(=O)C[C@H](O)[C@H]1OC(C)(C)O[C@@H]1[C@H](O)CN=[N+]=[N-]]

Compound (9b)

under the above same reaction conditions as the preparation of compound IXb.

The invention further relates to the use of the compound of formula IXb for the preparation of ammonium 8-azido-3,8-dideoxy-D-gluco-oct-2-ulosonate or 4eKdo-$N_3$ (10b):

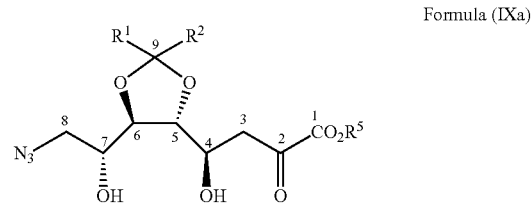

Compound (10b)

comprising deprotecting compound of formula IXb with an aqueous solution of an organic or inorganic acid.

According to a particular feature, the product of interest (10b) could be obtained by deprotection of compound of formula IXb (10 mg to 50 g) with an aqueous solution of an organic or inorganic acid (20 to 200 equivalents), such as acetic acid, trifluoroacetic acid, sulphuric acid, hydrochloric acid, preferably trifluoroacetic acid (5 to 30%, v/v), at a temperature between 0 and 80° C.

The invention further relates to the following new synthesis intermediate compound, which is claimed as new compound:

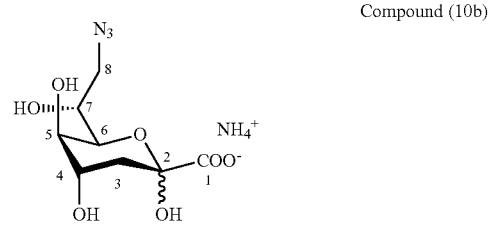

Formula (IXa)

Wherein:
$R^1$ and $R^2$ can be independently H; a $C_1$ to $C_6$ alkyl including methyl, ethyl, propyl, butyl; aryl including phenyl, paramethoxyphenyl; or $R^1$,$R^2$ together with the carbon C-6 can be a cyclopentylidene or cyclohexylidene; each of these groups being substituted or not;
and $R^5$ can be a $C_1$ to $C_6$ alkyl including methyl, ethyl, propyl, butyl, t-butyl, pentyl, hexyl; or benzyl; each of these groups being substituted or not.

More precisely, the invention relates to the specific synthesis intermediate compound (9a), which is claimed as new compound, named ethyl (4R)-4-{(4R,5R)-5-[(R)-2-azido-1-hydroxyethyl]-2,2-dimethyl-1,3-dioxolan-4-yl}-4-hydroxy-2-oxobutanoate (9a), here-below:

Compound (9a)

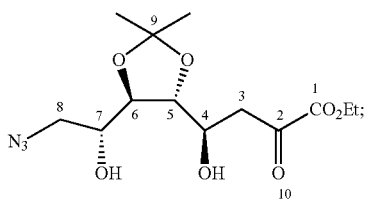

The invention further relates to the following new synthesis intermediate compound, which is claimed as new compound:

Formula (VIIIa)

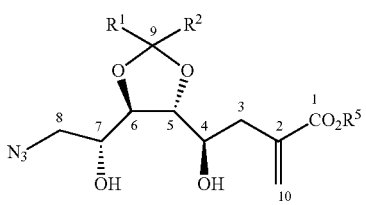

Wherein:
$R^1$ and $R^2$ can be independently H; a $C_1$ to $C_6$ alkyl including methyl, ethyl, propyl, butyl; aryl including phenyl, para-methoxyphenyl; or $R^1,R^2$ together with the carbon C-6 can be a cyclopentylidene or cyclohexylidene; each of these groups being substituted or not;
and $R^5$ can be a $C_1$ to $C_6$ alkyl including methyl, ethyl, propyl, butyl, t-butyl, pentyl, hexyl; or benzyl; each of these groups being substituted or not.

More precisely, the invention relates to the specific synthesis intermediate compound (8a), which is claimed as new compound, named ethyl (4R)-4-{(4R,5R)-5-[(R)-2-azido-1-hydroxyethyl]-2,2-dimethyl-1,3-dioxolan-4-yl)-4-hydroxy-2-methylenebutanoate (8a), here-below:

Compound (8a)

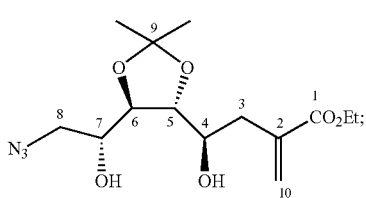

The invention further relates to the following new synthesis intermediate compound, which is claimed as new compound:

Formula (IXb)

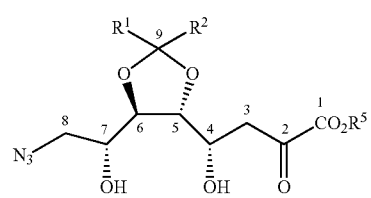

Wherein:
$R^1$ and $R^2$ can be independently H; a $C_1$ to $C_6$ alkyl including methyl, ethyl, propyl, butyl; aryl including phenyl, para-methoxyphenyl; or $R^1,R^2$ together with the carbon C-6 can be a cyclopentylidene or cyclohexylidene; each of these groups being substituted or not;
and $R^5$ can be a $C_1$ to $C_6$ alkyl including methyl, ethyl, propyl, butyl, t-butyl, pentyl, hexyl; or benzyl; each of these groups being substituted or not.

More precisely, the invention relates to the synthesis intermediate compound (9b), which is claimed as new compound, named ethyl (4S)-4-{(4R,5R)-5-[(R)-2-azido-1-hydroxyethyl]-2,2-dimethyl-1,3-dioxolan-4-yl}-4-hydroxy-2-oxobutanoate (9b), here-below:

Compound (9b)

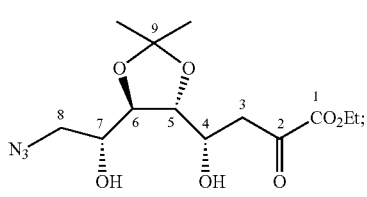

The invention further relates to the following new synthesis intermediate compound, which is claimed as new compound:

Formula (VIIIb)

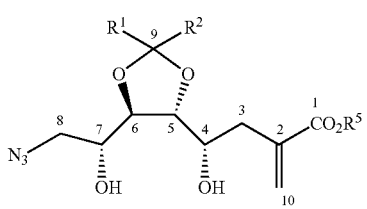

Wherein:
$R^1$ and $R^2$ can be independently H; a $C_1$ to $C_6$ alkyl including methyl, ethyl, propyl, butyl; aryl including phenyl, para-methoxyphenyl; or $R^1,R^2$ together with the carbon C-6 can be a cyclopentylidene or cyclohexylidene; each of these groups being substituted or not;
and $R^5$ can be a $C_1$ to $C_6$ alkyl including methyl, ethyl, propyl, butyl, t-butyl, pentyl, hexyl; or benzyl; each of these groups being substituted or not.

More precisely, the invention relates to the specific synthesis intermediate compound (8b), which is claimed as new compound, named ethyl (4S)-4-{(4R,5R)-5-[(R)-2-azido-1-hydroxyethyl]-2,2-dimethyl-1,3-dioxolan-4-yl}-4-hydroxy-2-methylenebutanoate (8b), here-below:

Compound (8b)

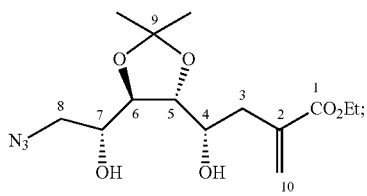

The invention further relates to the following new synthesis intermediate compound, which is claimed as new compound:

Formula (IV)

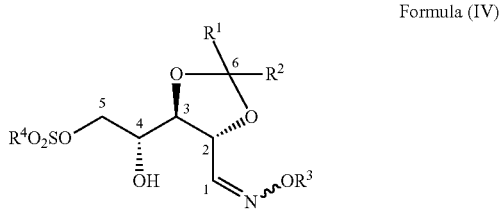

Wherein:
R¹ and R² can be independently H; a $C_1$ to $C_6$ alkyl including methyl, ethyl, propyl, butyl; aryl including phenyl, para-methoxyphenyl; or $R^1,R^2$ together with the carbon C-6 can be a cyclopentylidene or cyclohexylidene; each of these groups being substituted or not;
and R³ can be a $C_1$ to $C_6$ alkyl including methyl, ethyl, propyl, isopropyl, butyl, isobutyl, tert-butyl, pentyl; or aryl including phenyl, methylphenyl, ethylphenyl, each of these groups being substituted or not;
and R⁴ can be a $C_1$ to $C_6$ alkyl including methyl, ethyl, propyl; a $C_1$ to $C_6$ perfluoroalkyl including trifluoromethyl, pentafluoroethyl; or aryl including para-methylphenyl, para-nitrophenyl; each of these groups being substituted or not.

More precisely, the invention relates to the specific synthesis intermediate compound (4), which is claimed as new compound, named 2:3-isopropylidene-5-O-methanesulfonyl-D-arabinose O-methyloxime (4), here-below:

Compound (4)

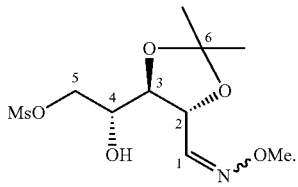

According to a further aspect, the invention relates to the use of some synthesis intermediates, and in particular of a compound of formula V or VI and in particular of formula (5) or (6), or of a compound of formula VIIIa or VIIIb, and in particular of formula (8a) or (8b), or of a compound of formula IXa or IXb, and in particular of formula (9a) or (9b), to detect bacteria, in particular Gram negative bacteria, including, without limitation, the following genus of bacteria: *Acinetobacter, Bacteroides, Bartonella, Bordetella, Brachyspira, Brucella, Burkholderia, Campylobacter, Cardiobacterium, Chlamydophila, Chryseobacterium, Clostridium, Coxiella, Cronobacter, Edwardsiella, Ehrlichia, Eikenella, Elizabethkingia, Enterobacter, Escherichia, Francisella, Fusobacterium, Haemophilus, Helicobacter, Klebsiella, Legionella, Leptospira, Morganella, Myxococcus, Neisseria, Neorickettsia, Pasteurella, Plesiomonas, Porphyromonas, Prevotella, Proteus, Providencia, Pseudoalteromonas, Pseudomonas, Rickettsia, Rhodocycclus, Salmonella, Serratia, Sinorhizobium, Shigella, Schewanella, Shewamma, Stenotrophomonas, Streptobacillus, Tenacibaculum, Treponema, Vibrio, Yersinia.*

According to the present invention, all the percentages are given by mol %, the temperature is in ° C., the pressure is atmospheric pressure, unless otherwise stated.

DETAILED DESCRIPTION OF THE BEST EMBODIMENT

According to the invention, and in reference to Scheme 1 here-below, the target compounds (10a) (8-azido-8-deoxy-Kdo) and (10b) (8-azido-8-deoxy-4eKdo) were synthesized in 11 steps from D-arabinose with an overall yield of 17 mol % and a purity of more than 95% for compound (10a) and 6 mol % overall yield and a purity of more than 95% for (10b). The key step in both syntheses is an indium-mediated allylation [1] of a common aldehyde intermediate (6) which in turn is obtained from an oxime ether intermediate [2]. And the target compound (7) (5-azido-Ara) was synthetized in 7 steps from D-arabinose with an overall yield of 26 mol % and a purity of more than 95%.

According to specific embodiments, the reaction of D-arabinose with O-methylhydroxylamine in dry pyridine afforded the corresponding O-methyloxime. The resulting intermediate was then protected into its bis-isopropylidene form compound (2) by reaction with 2,2-dimethoxypropane and a catalytic amount of p-toluenesulfonic acid. This compound was obtained as a mixture of E and Z-oxime ethers but no preparative purification was attempted since these oxime ethers were planned to be hydrolysed later.

Selective deprotection of the terminal acetonide in 80% aqueous acetic acid under reduced pressure (200 mbar) yielded compound (3) in 58% yield from D-arabinose. The azido derivative (5) was obtained by selective mesylation of the primary alcohol in pyridine followed by a nucleophilic substitution using sodium azide in dimethylformamide (78% over 2 steps).

To obtain the common aldehyde intermediate (6), a first attempted ozonolysis of oxime ethers (5) followed by reduction of unstable intermediates with dimethyl sulfide, yielded only 23% of compound (6) after chromatographic purification. Oxidative methods to regenerate the aldehyde from oximes using cerium ammonium nitrate [3] or a mixture of trimethylsilyl chloride and sodium nitrite [4] were unsuccessful.

Finally, target aldehyde (6) was obtained by hydrolysis of oxime ethers (5) in aqueous acetic acid by adding a stoichiometric amount of formaldehyde to trap the released O-methylhydroxylamine. This common intermediate (6) was first transformed into 5-azido-5-deoxy-D-arabinose (7) by removal of the isopropylidene group with a mixture of trifluoroacetic acid and water in dichloromethane. Hence, 5-azido-5-deoxy-D-arabinofuranose (7) was obtained in 58% from compound (5).

Barbier type indium-mediated allylation of aldehyde (6) with ethyl 2-(bromomethyl)acrylate gave the two erythro (8a) and threo (8b) diastereomers, the erythro isomer being the major product in a 2:1 ratio as predicted by Felkin-Anh model [5]. Confirmation of these absolute configurations was obtained by conversion of each diastereomer into compounds (10a) and (10b), respectively, and comparing their NMR spectra with that of previously synthesized 8-azido-8-deoxy-Kdo [6].

Hence, the two diastereomers were separated by flash chromatography over silica gel and each product was separately submitted to ozonolysis in methanol to provide after dimethylsufide addition, the alpha-keto esters (9a) and (9b), respectively. Final hydrolysis of the esters and the acetonides were achieved with 10% aqueous trifluoroacetic acid at 40° C. The instability of ulosonic acids to acidic conditions [7] made this step critical and evaporation of solvents had to be done on the rotary evaporator without warming followed by co-evaporation with toluene to allow complete elimination of the acid. Finally, the residue was neutralised with aqueous ammonia giving compounds (10a) and (10b) in 71% (from (8a)) and 46% (from (8b)) respectively. Compound (10a) proved to be identical to the previously reported 8-azido-3,8-dideoxy-D-manno-octulosonate.

This approach also afforded its 4-epimer, 8-azido-3,8-dideoxy-D-gluco-octulosonate (10b).

the invention and is claimed in all its aspects, in part or in combination.

SCHEME I

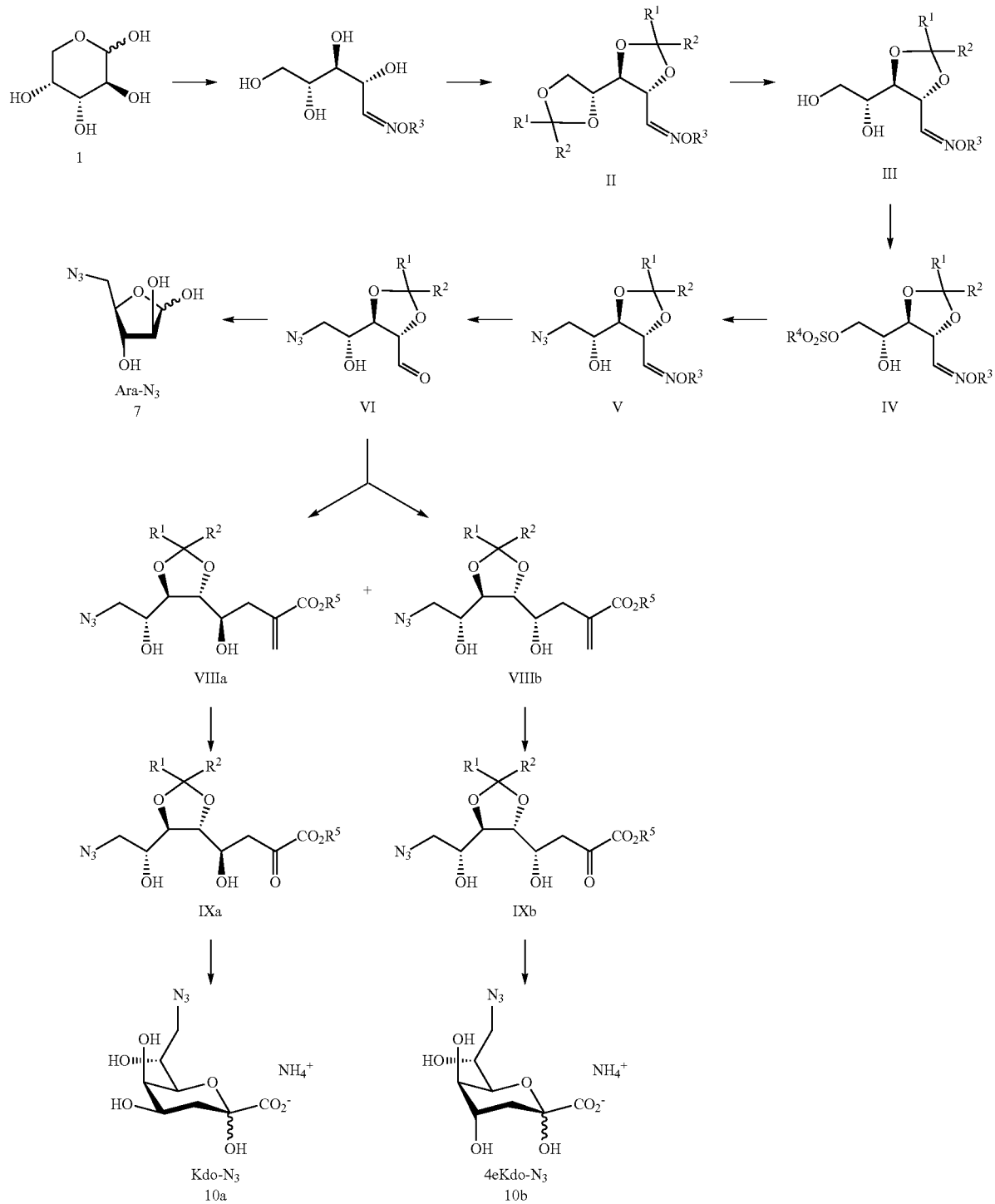

It is apparent that chemical reaction scheme I or scheme 1, here-below, starting from the commercially available D-arabinose to reach at will either known Kdo-N$_3$, or known 4eKdo-N$_3$ or even known Ara-N$_3$ forms an integral part of Wherein:

$R^1$ and $R^2$ can be independently H; a $C_1$ to $C_6$ alkyl including methyl, ethyl, propyl, butyl; aryl including phenyl, paramethoxyphenyl; or $R^1$,$R^2$ together with the carbon C-6 can be a cyclopentylidene or cyclohexylidene; each of these groups being substituted or not;

and $R^3$ can be a $C_1$ to $C_6$ alkyl including methyl, ethyl, propyl, isopropyl, butyl, isobutyl, tert-butyl, pentyl; or aryl including phenyl, methylphenyl, ethylphenyl, each of these groups being substituted or not;

and $R^4$ can be a $C_1$ to $C_6$ alkyl including methyl, ethyl, propyl; a $C_1$ to $C_6$ perfluoroalkyl including trifluoromethyl, pentafluoroethyl; or aryl including para-methylphenyl, para-nitrophenyl; each of these groups being substituted or not;

and $R^5$ can be a $C_1$ to $C_6$ alkyl including methyl, ethyl, propyl, butyl, pentyl, hexyl; each of these groups being substituted or not.

INVENTION EXAMPLES

Materials and Methods:

Thin layer chromatography was performed over Merck 60 F254 with detection by UV, and/or by charring with sulphuric acid or $KMnO_4$ or phosphomolybdic acid solutions. Silica gel 60 40-63 μm was used for flash column chromatography.

NMR spectra were taken on Bruker Avance 300 or 500 MHz spectrometers, using the residual protonated solvent as internal standard. Chemical shifts δ are given in parts per million (ppm) and coupling constants are reported as Hertz (Hz). Splitting patterns are designated as singlet (s), doublet (d), triplet (t), doublet of doublet (dd), doublet of doublet of doublet (ddd). Splitting patterns that could not be interpreted or easily visualized are designated as multiplet (m).

Mass spectra were taken on a Waters LCT Premier XE (ToF), with electrospray ionization in the positive (ESI+) or in the negative (ESI−) mode of detection.

IR-FT spectra were recorded on a Perkin Elmer Spectrum 100 spectrometer. Characteristic absorptions are reported in $cm^{-1}$.

Specific optical rotations were measured at 20° C. with an Anton Paar MCP 300 polarimeter in a 10-cm cell at 20° C. and 589 nm.

All biological and chemical reagents were of analytical or cell culture grade, obtained from commercial sources, and used without further purifications.

*Escherichia coli* and *Legionella* strains were purchased from ATCC-LGC or Leibniz Institute DSMZ (*E. coli* K12 ATCC 700926, *E. coli* O13 ATCC 15223, *Legionella pneumophila* Sg1 Philadelphia DSM 25020 and *Legionella* (*Fluoribacter*) *gormanii* ATCC 33342).

Fluorescence microscopy experiments were performed on a confocal straight Leica SP8 (DM 6000), using a 63× PLAN APO oil immersion lens (Leica), an argon laser (488 nm) and a GaAsP Hybrid detector (Hamamatsu). The microscope was operated with LAS-X program. ImageJ program was used for image treatment.

Invention Example 1

Synthesis of 5-azido-5-deoxy-2:3-isopropylidene-D-arabinose O-methyloxime (5)

Compound (5)

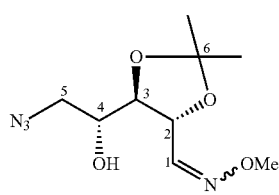

To a solution of (4E/4Z) (810 mg, 2.72 mmol, 1.0 eq.) in N,N-dimethylformamide (30.0 mL, 0.10 M), sodium azide (531 mg, 8.17 mmol, 3.0 eq.) was added and the reaction mixture was heated at 80° C. for 15 hours. Solvent was then removed under reduced pressure and the residue was purified by flash column chromatography (cyclohexane/ethyl acetate 9:1) to yield a mixture of 5-azido-5-deoxy-2:3-isopropylidene-D-arabinose O-methyloxime (5E/5Z) (NMR ratio 7:3, 637 mg, 96%) as yellowish oil. A fraction of (5E) was isolated by flash column chromatography (dichloromethane/MTBE 97:3) for its characterizations. Purity of more than 95% by NMR.

Rf (cyclohexane/ethyl acetate 8:2): 0.30.

IR ($cm^{-1}$): 3458, 2989, 2939, 2823, 2100, 1630, 1443, 1373, 1213, 1164, 1066, 1036, 885, 865.

HRMS (ESI$^+$): [M+H]$^+$ ($C_9H_{17}N_4O_4^+$) Calc. m/z: 245.1245, found: 245.1250.

Isomer (5E):

Rf (dichloromethane/MTBE 97:3): 0.23.

$^1$H-NMR (500 MHz, CDCl$_3$) δ: 7.42 (d, 1H, $J_{1,2}$ 5.8 Hz, H-1); 4.54 (dd, 1H, $J_{2,3}$ 7.2, $J_{1,2}$ 5.8 Hz, H-2); 3.98 (dd, 1H, $J_{2,3}$ 7.2, $J_{3,4}$ 6.4 Hz, H-3); 3.92 (dddd, 1H, $J_{3,4}$ 6.4, $J_{4,5b}$ 6.2, $J_{4,OH}$ 3.9, $J_{4,5a}$ 3.8 Hz, H-4); 3.85 (s, 3H, CH$_3$—O); 3.46 (dd, 1H, $J_{5a,5b}$ 12.5, $J_{4,5a}$ 3.8 Hz, H-5a); 3.42 (dd, 1H, $J_{5a,5b}$ 12.5, $J_{4,5b}$ 6.2 Hz, H-5b); 2.61 (d, 1H, $J_{4,OH}$ 3.9 Hz, OH); 1.41 (s, 3H, CH$_3$—C); 1.39 (s, 3H, CH$_3$—C).

$^{13}$C-NMR (125 MHz, CDCl$_3$) δ: 148.4 (C-1); 110.6 (C-6); 78.8 (C-3); 75.8 (C-2); 71.5 (C-4); 62.3 (CH$_3$—O); 53.7 (C-5); 27.0, 26.8 (2 CH$_3$—C).

Isomer (5Z):

$^1$H-NMR (500 MHz, CDCl$_3$) δ: 6.86 (d, 1H, $J_{1,2}$ 6.1 Hz, H-1); 4.94 (dd, 1H, $J_{2,3}$ 7.2, $J_{1,2}$ 6.1 Hz, H-2); 3.93 (s, 3H, CH$_3$—O); 3.87 (ddd, 1H, $J_{3,4}$ 7.5, $J_{4,5b}$ 6.4, $J_{4,5a}$ 2.8 Hz, H-4); 3.82 (dd, 1H, $J_{3,4}$ 7.5, $J_{2,3}$ 7.2 Hz, H-3); 3.47 (dd, 1H, $J_{5a,5b}$ 12.8, $J_{4,5a}$ 2.8 Hz, H-5a); 3.39 (dd, 1H, $J_{5a,5b}$ 12.8, $J_{4,5b}$ 6.4 Hz, H-5b); 1.40 (s, 3H, CH$_3$—C); 1.38 (s, 3H, CH$_3$—C).

$^{13}$C-NMR (75 MHz, CDCl$_3$) δ: 150.8 (C-1); 111.0 (C-6); 80.0 (C-3); 72.9 (C-2); 72.5 (C-4); 62.8 (CH$_3$—O); 53.5 (C-5); 26.9, 26.5 (2 CH$_3$—C).

Invention Example 2

Synthesis of 5-azido-5-deoxy-2:3-isopropylidene-D-arabinose (6)

Compound (6)

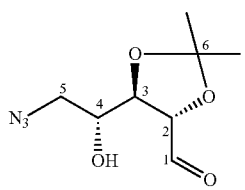

To a solution of (5E/5Z) (820 mg, 3.36 mmol, 1.0 eq.), as prepared from Example 1, in 80% (v/v) aqueous acetic acid (120 mL), formaldehyde (0.8 mL) was added and the reaction mixture was stirred for 1 hour at room temperature. Solvents were removed under reduced pressure and co-evaporation with toluene was done to assure complete elimination of acetic acid. The crude compound 5-azido-5-deoxy-2:3-isopropylidene-D-arabinose (6) (682 mg) was used directly in the next step without further purification. Colorless Oil Rf (cyclohexane/ethyl acetate 7:3): 0.56.

IR (cm$^{-1}$): 3408, 2988, 2936, 2100, 1733, 1440, 1373, 1238, 1213, 1164, 1063, 863.

$^1$H-NMR (500 MHz, CDCl$_3$) δ: 9.79 (d, 1H, J$_{1,2}$ 1.2 Hz, H-1); 4.41 (dd, 1H, J$_{2,3}$ 6.4, J$_{1,2}$ 1.2 Hz, H-2); 4.04 (dd, 1H, J$_{2,3}$ 6.4, J$_{3,4}$ 6.1 Hz, H-3); 3.90 (ddd, 1H, J$_{4,5b}$ 6.4, J$_{3,4}$ 6.1, J$_{4,5a}$ 3.4 Hz, H-4); 3.51 (dd, 1H, J$_{5a,5b}$ 12.8, J$_{4,5a}$ 3.4 Hz, H-5a); 3.43 (dd, 1H, J$_{5A,5B}$ 12.8, J$_{4,5B}$ 6.4 Hz, H-5B); 1.47 (s, 3H, CH$_3$—C); 1.37 (s, 3H, CH$_3$—C).

HRMS (ESI$^+$): [2M+Na]$^+$ (C$_{16}$H$_{26}$N$_6$NaO$_8$$^+$) Calc. m/z: 453.1704, found: 453.1726.

Invention Example 3

Synthesis of 2:3-isopropylidene-5-O-methanesulfonyl-D-arabinose O-methyloxime (4)

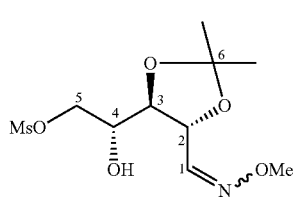

Compound (4)

To a solution of 2:3-isopropylidene-D-arabinose O-methyloxime (3) (3E/3Z) (100 mg, 0.46 mmol, 1.0 eq.) in dry pyridine (2.0 mL) at −20° C., mesyl chloride (0.10 mL, 1.37 mmol, 3.0 eq.) was added and the reaction mixture was stirred for 1.5 hours at −20 C. After quenching the reaction with CH$_3$OH (0.3 mL), solvents were removed under vacuum. The resulting residue was purified by silica flash column chromatography (cyclohexane/ethyl acetate 6:4) to yield a mixture of 2:3-isopropylidene-5-O-methanesulfonyl-D-arabinose O-methyloxime (4E/4Z) (NMR ratio 4:1, 110 mg, 81%) as colorless oil. An aliquot of pure (4E) isomer was obtained by flash column chromatography (dichloromethane/diethyl ether 9:1) and characterized. Purity of more than 95% by NMR.

Rf (cyclohexane/ethyl acetate 6:4): 0.24.

IR (cm$^{-1}$): 3500, 2989, 2941, 2824, 1631, 1458, 1350, 1215, 1170, 1067, 1033, 959, 887, 863, 833.

HRMS (ESI$^+$): [M+H]$^+$ (C$_{10}$H$_{20}$NO$_7$S$^+$) Calc. m/z: 298.0955, found: 298.0947.

Isomer (4E):

Rf (cyclohexane/ethyl acetate 6:4): 0.20.

$^1$H-NMR (500 MHz, CDCl$_3$) δ: 7.42 (d, 1H, J$_{1,2}$ 5.6 Hz, H-1); 4.56 (dd, 1H, J$_{2,3}$ 6.8, J$_{1,2}$ 5.6 Hz, H-2); 4.41 (dd, 1H, J$_{5a,5b}$ 11.0, J$_{4,5a}$ 2.7 Hz, H-5a); 4.28 (dd, 1H, J$_{5a,5b}$ 11.0, J$_{4,5b}$ 5.7 Hz, H-5b); 4.03 (ddd, 1H, J$_{3,4}$ 7.0, J$_{4,5b}$ 5.7, J$_{4,5a}$ 2.7 Hz, H-4); 4.01 (dd, 1H, J$_{2,3}$ 6.8, J$_{3,4}$ 7.0 Hz, H-3); 3.85 (s, 3H, CH$_3$—O); 3.06 (s, 3H, CH$_3$—S); 1.41 (s, 3H, CH$_3$—C); 1.39 (s, 3H, CH$_3$—C).

$^{13}$C-NMR (125 MHz, CDCl$_3$) δ: 148.2 (C-1); 110.9 (C-6); 77.9 (C-3); 76.2 (C-2); 70.9 (C-5); 70.8 (C-4); 62.3 (CH$_3$—O); 37.8 (CH$_3$—S); 27.0, 26.9 (2 CH$_3$—C).

Isomer (4Z):

$^1$H-NMR (300 MHz, CDCl$_3$) δ: 6.87 (d, 1H, J$_{1,2}$ 5.9 Hz, H-1); 4.96 (dd, 1H, J$_{2,3}$ 7.3, J$_{1,2}$ 5.9 Hz, H-2); 4.45 (dd, 1H, J$_{5a,5b}$ 11.4, J$_{4,5a}$ 2.4 Hz, H-5a); 4.29 (dd, 1H, J$_{5a,5b}$ 11.4, J$_{4,5b}$ 7.9 Hz, H-5b); 3.98 (ddd, 1H, J$_{4,5b}$ 7.9, J$_{4,3}$ 7.5, J$_{4,5a}$ 2.4 Hz, H-4); 3.93 (s, 3H, CH$_3$—O); 3.84 (dd, 1H, J$_{3,4}$ 7.5, J$_{3,2}$ 7.3 Hz, H-3); 3.06 (s, 3H, CH$_3$—S); 1.40 (s, 3H, CH$_3$—C); 1.39 (s, 3H, CH$_3$—C).

$^{13}$C-NMR (75 MHz, CDCl$_3$) δ: 150.7 (C-1); 111.2 (C-6); 79.1 (C-3); 72.9 (C-2); 71.3 (C-5); 70.9 (C-4); 62.9 (CH$_3$—O); 37.9 (CH$_3$—S); 27.0, 26.6 (2 CH$_3$—C).

Invention Example 4

Synthesis of 2:3-isopropylidene-D-arabinose O-methyloxime (3)

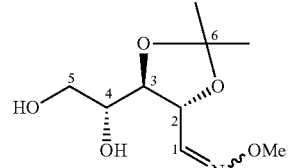

Compound (3)

A solution of 2:3,4:5-diisopropylidene-D-arabinose O-methyloxime (2) (2E/2Z) and impurity (1.50 g) in 80% (v/v) aqueous acetic acid (30 mL) was heated to 40° C. at 200 mbar of pressure on a rotavap. After 2.5 hours solvents were removed under reduced pressure and the residue was co-evaporated with toluene. A mixture of isomers 2:3-isopropylidene-D-arabinose O-methyloxime (3E/3Z) (NMR ratio 4:1, 876 mg, 58% over 3 steps) were obtained after silica gel flash column chromatography (cyclohexane/ethyl acetate 1:1) as colorless oil. Purity of more than 95% by NMR.

Rf (cyclohexane/ethyl acetate 1:1): 0.24.

IR (cm$^{-1}$): 3409, 2939, 1373, 1216, 1040, 885.

HRMS (ESI$^+$): [M+H]$^+$ (C$_9$H$_{18}$NO$_5$$^+$) Calc. m/z: 220.1179, found: 220.1184.

Isomer (3E):

$^1$H-NMR (500 MHz, CDCl$_3$) δ: 7.44 (d, 1H, J$_{1,2}$ 5.5 Hz, H-1); 4.56 (dd, 1H, J$_{2,3}$ 7.4, J$_{1,2}$ 5.5 Hz, H-2); 4.07 (dd, 1H, J$_{2,3}$ 7.4, J$_{3,4}$ 5.6 Hz, H-3); 4.13 (ddd, 1H, J$_{3,4}$ 5.6, J$_{4,5}$ 5.1, J$_{4,5}$ 4.7 Hz, H-4); 3.84 (s, 3H, CH$_3$—O); 3.72-3.68 (m, 2H, 2H-5); 1.42 (s, 3H, CH$_3$—C); 1.38 (s, 3H, CH$_3$—C).

$^{13}$C-NMR (125 MHz, CDCl$_3$) δ: 149.1 (C-1); 110.3 (C-6); 79.4 (C-3); 75.0 (C-2); 71.6 (C-4); 63.4 (C-5); 62.2 (CH$_3$—O); 26.9, 26.7 (2 CH$_3$—C).

Isomer (3Z):

$^1$H-NMR (500 MHz, CDCl$_3$) δ: 6.86 (d, 1H, J$_{1,2}$ 5.9 Hz, H-1); 4.95 (dd, 1H, J$_{2,3}$ 7.7, J$_{1,2}$ 5.9 Hz, H-2); 3.92 (s, 3H, CH$_3$—O); 3.87 (dd, 1H, J$_{2,3}$ 7.7, J$_{3,4}$ 6.9 Hz, H-3); 3.82-3.75 (m, 2H, H-4, H-5a); 3.72-3.68 (m, 1H, H-5b); 1.40 (2s, 6H, 2 CH$_3$—C).

$^{13}$C-NMR (125 MHz, CDCl$_3$) δ: 151.0 (C-1); 110.9 (C-6); 80.4 (C-3); 72.9 (C-2); 72.7 (C-4); 63.5 (C-5); 62.8 (CH$_3$—O); 27.0, 26.5 (2 CH$_3$—C).

Invention Example 5

Synthesis of 2:3,4:5-diisopropylidene-D-arabinose O-methyloxime (2) from D-(−)-arabinose Compound (2)

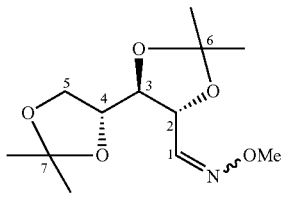

To a solution of D-(−)-arabinose (4.00 g, 26.6 mmol, 1.0 eq.) in dry pyridine (90 mL) was added methoxyamine hydrochloride (2.72 g, 32.0 mmol, 1.2 eq.) and the mixture was stirred at room temperature for 15 hours. Solvents were removed under reduced pressure and the residue was co-evaporated with toluene three times. The residue was resuspended in 2,2-dimethoxypropane (100 mL) and p-toluenesulfonic acid (1.01 g, 5.33 mmol, 0.2 eq.) was added and the suspension was heated to reflux for 4 hours followed by further 15 hours of stirring at room temperature. The reaction mixture was filtered over Celite® and solvents were evaporated. The residue was dissolved in ethyl acetate (200 mL) and was washed with saturated aq. NaCl solution (2×150 mL). Purification by silica flash column chromatography (cyclohexane/ethyl acetate 9:1) yields a mixture of isomers 2:3,4:5-diisopropylidene-D-arabinose O-methyloxime (2E/2Z) and an unknown impurity (NMR ratio 6:1:0.4, 5.83 g) as colorless oil. This mixture was used without further purification in the next step. An aliquot of pure (2E) was obtained by a second flash column chromatography (dichloromethane/MTBE 98:2) and characterized.

Isomer (2E):

Rf (CH$_2$Cl$_2$/MTBE 98:2): 0.35.

IR (cm$^{-1}$): 2987, 2939, 2900, 2821, 1631, 1456, 1381, 1371, 1241, 1212, 1150, 1065, 1038, 887, 842.

$^1$H-NMR (500 MHz, CDCl$_3$) δ: 7.35 (d, 1H, J$_{1,2}$ 6.3 Hz, H-1); 4.46 (dd, 1H, J$_{2,3}$ 7.1, J$_{1,2}$ 6.3 Hz, H-2); 4.13 (ddd, 1H, J$_{3,4}$ 6.9, J$_{4,5a}$ 6.1, J$_{4,5b}$ 4.8 Hz, H-4); 4.08 (dd, 1H, J$_{5a,5b}$ 8.5, J$_{4,5a}$ 6.1 Hz, H-5a); 3.97 (d, 1H, J$_{2,3}$ 7.1, J$_{3,4}$ 6.9 Hz, H-3); 3.94 (dd, 1H, J$_{5a,5b}$ 8.5, J$_{4,5b}$ 4.8 Hz, H-5b); 3.85 (s, 3H, CH$_3$—O); 1.40 (s, 3H, CH$_3$—C); 1.38 (s, 6H, 2 CH$_3$—C); 1.32 (s, 3H, CH$_3$—C).

$^{13}$C-NMR (125 MHz, CDCl$_3$) δ: 147.8 (C-1); 110.8 (C-6); 110.0 (C-7); 79.4 (C-3); 76.7 (C-2); 76.6 (C-4); 67.1 (C-5); 62.1 (CH$_3$—O); 27.1, 27.0, 26.9, 25.4 (4 CH$_3$—C).

HRMS (ESI$^+$): [M+H]$^+$ (C$_{12}$H$_{22}$NO$_5{}^+$) Calc. m/z: 260.1492, found: 260.1502.

Invention Example 6

Use of 5-azido-5-deoxy-2:3-isopropylidene-D-arabinose for the synthesis of 5-azido-5-deoxy-D-arabinofuranose or Ara-N$_3$ (7)

Compound (7)

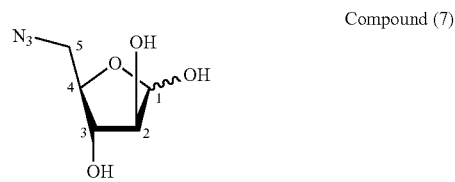

To a solution of crude 5-azido-5-deoxy-2:3-isopropylidene-D-arabinose (6) (100 mg), obtained in invention Example 2 above, in a mixture of CH$_2$Cl$_2$/H$_2$O (20:1, 21 mL), trifluoroacetic acid (1 mL) was added and the mixture was stirred at room temperature for 1 hour. Solvents were then evaporated, the crude residue was resuspended in water and lyophilized. After silica flash column chromatography (dichloromethane/methanol 92:8), the compound 5-azido-5-deoxy-D-arabinofuranose or Ara-N$_3$ (7) (50 mg, 58% over 2 steps from compound (5)) was obtained as a mixture of α/β anomers (NMR ratio 55:45) as a colorless oil. Purity of more than 95% by NMR.

Rf (dichloromethane/methanol 92:8): 0.28.

IR (cm$^{-1}$): 3367, 2106, 1281, 1040.

HRMS (ESI$^+$): [M+H−N$_2$]+(C$_5$H$_{10}$NO$_4{}^+$) Calc. m/z: 148.0604, found: 148.0610.

Anomer Alpha (7α):

$^1$H-NMR (500 MHz, D$_2$O) δ: 5.24 (d, 1H, J$_{1,2}$ 2.9 Hz, H-1); 4.17 (ddd, 1H, J$_{3,4}$ 6.4, J$_{4,5b}$ 5.8, J$_{4,5a}$ 3.5 Hz, H-4); 4.01 (dd, 1H, J$_{2,3}$ 4.6, J$_{1,2}$ 2.9 Hz, H-2); 3.97 (dd, 1H, J$_{3,4}$ 6.4, J$_{3,2}$ 4.6 Hz, H-3); 3.64 (dd, 1H, J$_{5a,5b}$ 13.6, J$_{4,5a}$ 3.5 Hz, H-5a); 3.44 (dd, 1H, J$_{5a,5b}$ 13.6, J$_{4,5b}$ 5.8 Hz, H-5b).

$^{13}$C-NMR (125 MHz, D$_2$O) δ: 101.0 (C-1); 81.3 (C-4); 81.2 (C-2); 76.3 (C-3); 51.5 (C-5).

Anomer Beta (7β):

$^1$H-NMR (500 MHz, D$_2$O) δ: 5.28 (br d, 1H, J$_{1,2}$ 3.1 Hz, H-1); 4.10-4.05 (m, 2H, H-2, H-3); 3.89 (ddd, 1H, J$_{3,4}$-7.1, J$_{4,5b}$ 6.5, J$_{4,5a}$ 3.5 Hz, H-4); 3.59 (dd, 1H, J$_{5a,5b}$ 13.3, J$_{4,5a}$ 3.5 Hz, H-5a); 3.42 (dd, 1H, J$_{5a,5b}$ 13.3, J$_{4,5b}$ 6.5 Hz, H-5b).

$^{13}$C-NMR (125 MHz, D$_2$O) δ: 95.2 (C-1); 79.6 (C-4); 75.8 (C-2); 74.7 (C-3); 52.6 (C-5).

Invention Example 7

Use of 5-azido-5-deoxy-2:3-isopropylidene-D-arabinose for the synthesis of ethyl (4R)-4-4-{(4R,5R)-5-[(R)-2-azido-1-hydroxyethyl]-2,2-dimethyl-1,3-dioxolan-4-yl)-4-hydroxy-2-methylenebutanoate (8a)

Compound (8a)

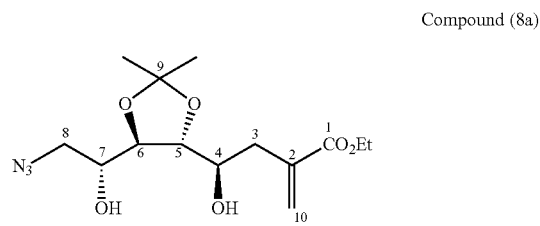 [SMILES: C=C(C[C@@H](O)[C@H]1OC(C)(C)O[C@@H]1[C@H](O)CN=[N+]=[N-])C(=O)OCC]

To a solution of 5-azido-5-deoxy-2:3-isopropylidene-D-arabinose (6) (40 mg), obtained in invention Example 2 above, in $CH_3CN/H_2O$ (1:1, 18.0 mL, 0.01 M) at 0° C., ethyl 2-(bromomethyl) acrylate (0.085 mL, 0.61 mmol, 3.3 eq.) and aqueous formic acid (10%, 0.19 mL) were added and the reaction mixture was allowed to stir for 10 min at 0° C. Indium powder (23 mg, 0.20 mmol, 1.1 eq.) was then added and the reaction mixture was stirred for 3 hours while temperature was maintained between 0-5° C. After filtration, solvents were evaporated under reduced pressure and the resulting mixture was purified by flash column chromatography (cyclohexane/ethyl acetate 75:25) to afford compound (8a) (33 mg, 54%) as colorless oil. Purity of more than 95% by NMR.

Rf (cyclohexane/ethyl acetate 7:3): 0.22.

IR $(cm^{-1})$: 3397, 2986, 2935, 2101, 1710, 1629, 1444, 1371, 1211, 1162, 1068, 1026, 949, 872.

$^1$H-NMR (500 MHz, $CDCl_3$) δ: 6.29 (d, 1H, $J_{10a,10b}$ 1.1 Hz, H-10a); 5.79 (d, 1H, $J_{10a,10b}$ 1.1 Hz, H-10b); 4.92 (br s, 1H, OH); 3.38 (br s, 1H, OH); 4.24 (q, 2H, $^3J$ 7.2 Hz, $OCH_2CH_3$); 3.83 (dd, 1H, $J_{6,7}$ 8.4, $J_{5,6}$ 7.4 Hz, H-6); 3.72 (ddd, 1H, $J_{6,7}$ 8.4, $J_{7,8b}$ 5.3, $J_{7,8a}$ 2.7 Hz, H-7); 3.68 (ddd, 1H, $J_{4,5}$ 8.9, $J_{4,3b}$ 7.5, $J_{4,3a}$ 2.2 Hz, H-4); 3.60 (dd, 1H, $J_{5,4}$ 8.9, $J_{5,6}$ 7.4 Hz, H-5); 3.52 (dd, 1H, $J_{8a,8b}$ 12.6, $J_{7,8a}$ 2.7 Hz, H-8a); 3.36 (dd, 1H, $J_{8a,8b}$ 12.6, $J_{7,8b}$ 5.3 Hz, H-8b); 2.87 (dd, 1H, $J_{3a,3b}$ 14.4, $J_{4,3a}$ 2.2 Hz, H-3a); 2.49 (dd, 1H, $J_{3a,3b}$ 14.4, $J_4$,3b 7.5 Hz, H-3b); 1.35 (s, 3H, $CH_3$—C); 1.33 (s, 3H, $CH_3$—C); 1.31 (t, 3H, $^3J$ 7.2 Hz, $OCH_2CH_3$).

$^{13}$C-NMR (75 MHz, $CDCl_3$) δ: 170.0 (C-1); 136.8 (C-2); 129.6 (C-10); 109.4 (C-9); 82.3 (C-5); 80.7 (C-6); 73.1 (C-4); 72.7 (C-7); 62.1 ($OCH_2CH_3$); 54.3 (C-8); 37.4 (C-3); 27.0 (2 $CH_3$); 14.3 ($OCH_2CH_3$).

HRMS ($ESI^+$): $[M+H]^+$ ($C_{14}H_{24}N_3O_6^+$) Calc. m/z: 330.1660, found: 330.1670.

$[\alpha]_D$=+18.0 (c 1.0, $CHCl_3$).

Invention Example 8

Use of 5-azido-5-deoxy-2:3-isopropylidene-D-arabinose for the synthesis of ethyl (4S)-4-{(4R,5R)-5-[(R)-2-azido-1-hydroxyethyl]-2,2-dimethyl-1,3-dioxolan-4-yl)-4-hydroxy-2-methylenebutanoate (8b)

Compound (8b)

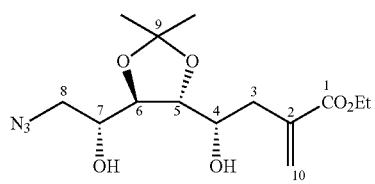

To a solution of 5-azido-5-deoxy-2:3-isopropylidene-D-arabinose (6) (40 mg) in $CH_3CN/H_2O$ (1:1, 18.0 mL, 0.01 M) at 0° C., ethyl 2-(bromomethyl) acrylate (0.085 mL, 0.61 mmol, 3.3 eq.) and aqueous formic acid (10%, 0.19 mL) were added and the reaction mixture was allowed to stir for 10 min at 0° C. Indium powder (23 mg, 0.20 mmol, 1.1 eq.) was then added and the reaction mixture was stirred for 3 hours while temperature was maintained between 0-5° C. After filtration, solvents were evaporated under reduced pressure and the resulting mixture was purified by flash column chromatography (cyclohexane/ethyl acetate 75:25) to afford ethyl (4S)-4-{(4R,5R)-5-[(R)-2-azido-1-hydroxyethyl]-2,2-dimethyl-1,3-dioxolan-4-yl)-4-hydroxy-2-methylenebutanoate (8b) (17 mg, 28%) as colorless oil. Purity of more than 95% by NMR.

Rf (cyclohexane/ethyl acetate 7:3): 0.19.

IR $(cm^{-1})$: 3397, 2986, 2935, 2101, 1710, 1629, 1444, 1371, 1211, 1162, 1068, 1026, 949, 872.

$^1$H-NMR (500 MHz, $CDCl_3$) δ: 6.24 (d, 1H, $J_{10a,10b}$ 0.9 Hz, H-10a); 5.71 (d, 1H, $J_{10a,10b}$ 0.9 Hz, H-10b); 4.21 (q, 2H, 317.1 Hz, $OCH_2CH_3$); 4.00 (dd, 1H, $J_{5,6}$ 7.8, $J_{4,5}$ 3.0 Hz, H-5); 3.93 (dddd, 1H, $J_{3b,4}$ 9.0, $J_{4,OH}$ 5.6, $J_{4,5}$ 3.0, $J_{4,3a}$ 3.0 Hz, H-4); 3.89 (dd, 1H, $J_{6,7}$ 7.9, $J_{5,6}$ 7.8 Hz, H-6); 3.75 (dddd, 1H, $J_{6,7}$ 7.9, $J_{7,8b}$ 6.1, $J_{7,8a}$ 2.8, $J_{7,OH}$ 2.5 Hz, H-7); 3.55 (dd, 1H, $J_{8a,8b}$ 12.6, $J_{7b,8a}$ 2.8 Hz, H-8a); 3.46 (br d, 1H, $J_{4,OH}$ 5.6 Hz, OH(4)); 3.40 (dd, 1H, $J_{8a,8b}$ 12.6, $J_{7,8b}$ 6.1 Hz, H-8b); 3.38 (br d, 1H, $J_{4,OH}$ 2.5 Hz, OH(7)); 2.66 (dd, 1H, $J_{3a,3b}$ 14.4, $J_{4,3a}$ 3.0 Hz, H-3a); 2.50 (dd, 1H, $J_{3a,3b}$ 14.4, $J_{4,3b}$ 9.0 Hz, H-3b); 1.40 (s, 3H, $CH_3$—C); 1.35 (s, 3H, $CH_3$—C); 1.29 (t, 3H, $^3J$7.1 Hz, $OCH_2CH_3$).

$^{13}$C-NMR (75 MHz, $CDCl_3$) δ: 168.4 (C-1); 137.7 (C-2); 128.3 (C-10); 109.7 (C-9); 81.8 (C-5); 76.8 (C-6); 72.6 (C-7); 69.9 (C-4); 61.5 ($OCH_2CH_3$); 54.4 (C-8); 37.0 (C-3); 27.2 (2 $CH_3$); 14.3 ($OCH_2CH_3$).

HRMS ($ESI^+$): $[M+H]^+$ ($C_{14}H_{24}N_3O_6^+$) Calc. m/z: 330.1660, found: 330.1670.

$[\alpha]_D$=+7.7 (c 1.0, $CHCl_3$).

Invention Example 9

Use of ethyl (4R)-4-{(4R,5R)-5-[(R)-2-azido-1-hydroxyethyl]-2,2-dimethyl-1,3-dioxolan-4-yl)-4-hydroxy-2-methylenebutanoate (8a) for the synthesis of ethyl (4R)-4-{(4R,5R)-5-[(R)-2-azido-1-hydroxyethyl]-2,2-dimethyl-1,3-dioxolan-4-yl}-4-hydroxy-2-oxobutanoate (9a)

Compound (9a)

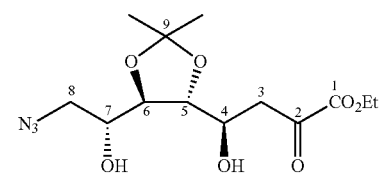

A solution of ethyl (4R)-4-{(4R,5R)-5-[(R)-2-azido-1-hydroxyethyl]-2,2-dimethyl-1,3-dioxolan-4-yl)-4-hydroxy-2-methylenebutanoate (8a) (120 mg, 0.36 mmol, 1.0 eq.) in $CH_3OH$ (18 mL, 0.02 M), as obtained from invention Example 7 above, at −78° C. was bubbled with ozone ($O_3$) for 15 min. The solution was purged with oxygen for 2 min until the blue color disappeared and then was degassed with argon for 5 min. An excess of dimethyl sulfide (0.1 mL, 1.36 mmol, 3.8 eq.) was added and the mixture was stirred at room temperature for 2 hours. After solvents evaporation, the residue was extracted with $Et_2O$ (3×10 mL) and the organic phases were washed with brine (2×10 mL), dried over anhydrous $MgSO_4$ and concentrated under reduced pressure. Ethyl (4R)-4-{(4R,5R)-5-[(R)-2-azido-1-hydroxyethyl]-2,2-dimethyl-1,3-dioxolan-4-yl}-4-hydroxy-2-oxobutanoate (9a) (97 mg) was used for the next step without further purification.

Colourless Oil

Rf (cyclohexane/ethyl acetate 1:1): 0.40

IR (cm$^{-1}$): 3377, 2988, 2103, 1729, 1443, 1373, 1257, 1164, 871.

$^1$H-NMR (500 MHz, CDCl$_3$) δ: 4.32 (q, 2H, $^3$J 7.2 Hz, OCH$_2$CH$_3$); 4.15 (ddd, 1H, J$_{3b,4}$ 8.8, J$_{4,5}$ 8.6, J$_{4,3a}$ 3.1 Hz, H-4); 3.84 (dd, 1H, J$_{6,7}$ 8.2, J$_{5,6}$ 7.3 Hz, H-6); 3.74 (dd, 1H, J$_{4,5}$ 8.6, J$_{5,6}$ 7.3 Hz, H-5); 3.74 (ddd, 1H, J$_{6,7}$ 8.2, J$_{7,8b}$ 5.7, J$_{7,8a}$ 2.8 Hz, H-7); 3.59 (dd, 1H, J$_{8a,8b}$ 12.6, J$_{7,8a}$ 2.68 Hz, H-8a); 3.40 (dd, 1H, J$_{8a,8b}$ 12.6, J$_{7,8b}$ 5.7 Hz, H-8b); 3.40 (dd, 1H, J$_{3a,3b}$ 18.2, J$_{4,3a}$ 3.1 Hz, H-3a); 3.01 (dd, 1H, J$_{3a,3b}$ 18.2, J$_{4,3b}$ 8.8 Hz, H-3b); 1.36 (t, 3H, $^3$J 7.2 Hz, OCH$_2$CH$_3$); 1.34 (s, 3H, CH$_3$); 1.33 (s, 3H, CH$_3$).

$^{13}$C-NMR (125 MHz, CDCl$_3$) δ: 194.0 (C-2); 160.7 (C-1); 110.1 (C-9); 82.1 (C-5); 80.6 (C-6); 72.6 (C-7); 69.6 (C-4); 63.1 (OCH$_2$CH$_3$); 54.3 (C-8); 44.2 (C-3); 27.0, 26.9 (2 CH$_3$); 14.2 (OCH$_2$CH$_3$).

HRMS (ESI$^+$): [2M+Na]$^+$ (C$_{26}$H$_{42}$N$_6$NaO$_{14}$$^+$) Calc. m/z: 685.2651, found: 685.2656.

[α]$_D$=+39.5 (c 1.0, CHCl$_3$).

Invention Example 10

Use of ethyl (4S)-4-4-{(4R,5R)-5-[(R)-2-azido-1-hydroxyethyl]-2,2-dimethyl-1,3-dioxolan-4-yl)-4-hydroxy-2-methylenebutanoate (8b) for the synthesis of ethyl (4S)-4-{(4R,5R)-5-[(R)-2-azido-1-hydroxyethyl]-2,2-dimethyl-1,3-dioxolan-4-yl}-4-hydroxy-2-oxobutanoate (9b)

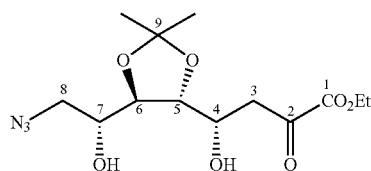

Compound (9b)

A solution of ethyl (4S)-4-{(4R,5R)-5-[(R)-2-azido-1-hydroxyethyl]-2,2-dimethyl-1,3-dioxolan-4-yl)-4-hydroxy-2-methylenebutanoate (8b) (70 mg, 0.21 mmol, 1.0 eq.), as obtained from invention Example 8, in CH$_3$OH (10.0 mL, 0.02 M) at −78° C. was bubbled with ozone (O$_3$) for 15 min. The solution was purged with oxygen for 2 min until the blue color disappeared and then was degassed with argon for 5 min. An excess of dimethyl sulfide (0.1 mL, 1.36 mmol, 6.5 eq.) was added and the mixture was stirred at room temperature for 2 hours. After solvents evaporation, the residue was extracted with Et$_2$O (3×5 mL) and the organic phases were washed with brine (2×5 mL), dried over anhydrous MgSO$_4$ and concentrated under reduced pressure. Ethyl (4S)-4-{(4R,5R)-5-[(R)-2-azido-1-hydroxyethyl]-2,2-dimethyl-1,3-dioxolan-4-yl}-4-hydroxy-2-oxobutanoate (9b) (45 mg) was used for the next step without further purification.

Colourless Oil

Rf (cyclohexane/ethyl acetate 1:1): 0.41.

IR (cm$^{-1}$): 3443, 2989, 2104, 1731, 1373, 1256, 1069, 870.

$^1$H-NMR (500 MHz, CDCl$_3$) δ: 4.38 (ddd, 1H, J$_{3a,4}$ 8.2, J$_{4,3b}$ 4.2, J$_{4,5}$ 3.1 Hz, H-4); 4.32 (q, 2H, $^3$J 7.2 Hz, OCH$_2$CH$_3$); 4.01 (dd, 1H, J$_{5,6}$ 7.7, J$_{4,5}$ 3.1 Hz, H-5); 3.90 (dd, 1H, J$_{6,7}$ 8.0, J$_{5,6}$ 7.7 Hz, H-6); 3.76 (ddd, 1H, J$_{6,7}$ 8.0, J$_{7,8b}$ 6.3, J$_{7,8a}$ 3.0 Hz, H-7); 3.59 (dd, 1H, J$_{8a,8b}$ 12.6, J$_{7,8a}$ 3.0 Hz, H-8a); 3.43 (dd, 1H, J$_{8a,8}$b 12.6, J$_{7,8b}$ 6.3 Hz, H-8b); 3.20 (dd, 1H, J$_{3a,3b}$ 17.4, J$_{4,3a}$ 8.2 Hz, H-3a); 3.11 (dd, 1H, J$_{3a,3b}$ 17.4, J$_{4,3b}$ 4.2 Hz, H-3b); 1.39 (s, 3H, CH$_3$—C); 1.36 (t, 3H, $^3$J 7.2 Hz, OCH$_2$CH$_3$); 1.35 (s, 3H, CH$_3$—C).

$^{13}$C-NMR (125 MHz, CDCl$_3$) δ: 193.4 (C-2); 160.8 (C-1); 110.0 (C-9); 81.6 (C-5); 76.6 (C-6); 72.6 (C-7); 66.6 (C-4); 63.0 (OCH$_2$CH$_3$); 54.5 (C-8); 43.2 (C-3); 27.2, 27.0 (2 CH$_3$); 14.2 (OCH$_2$CH$_3$).

HRMS (ESI$^+$): [2M+Na]$^+$ (C$_{26}$H$_{42}$N$_6$O$_{14}$Na$^+$) Calc. m/z: 685.2651, found: 685.2672.

[α]$_D$=−0.6 (c 1.0, CHCl$_3$).

Invention Example 11

Use of ethyl (4R)-4-4-{(4R,5R)-5-[(R)-2-azido-1-hydroxyethyl]-2,2-dimethyl-1,3-dioxolan-4-yl}-4-hydroxy-2-oxobutanoate (9a) for the synthesis of ammonium 8-azido-3,8-dideoxy-D-manno-oct-2-ulosonate (Kdo-N$_3$) (10a)

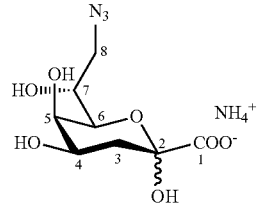

Compound (10a)

To a solution of crude ethyl (4R)-4-{(4R,5R)-5-[(R)-2-azido-1-hydroxyethyl]-2,2-dimethyl-1,3-dioxolan-4-yl}-4-hydroxy-2-oxobutanoate (9a) (90 mg) in water (22.5 mL) as obtained from invention Example 9, trifluoroacetic acid (2.5 mL) was added and the mixture was stirred at 40° C. for 2 hours. Solvents were removed under reduced pressure without warming the bath and then co-evaporated twice with toluene to assure complete removal of acid. The residue was neutralized with ammonia (0.2 mol·L$^{-1}$) and then concentrated. Purification by flash column chromatography (ethyl acetate/ethanol/water 65:30:5) gave pure ammonium 8-azido-3,8-dideoxy-D-manno-oct-2-ulosonate or Kdo-N$_3$ (10a) (67 mg, 71% starting from (8a)) as yellowish foam. Purity of more than 95% by NMR.

Rf (ethyl acetate/ethanol/water 65:30:5): 0.20.

IR (cm$^{-1}$): 3297, 2934, 2107, 1610, 1417, 1284, 1076, 756.

HRMS (ESI$^-$): [M-NH$_4$]$^-$ (C$_8$H$_{12}$N$_3$O$_7$$^-$) Calc. m/z: 262.0681, found: 262.0685.

Major Conformer Alpha Pyranose Form (NMR 16):

$^1$H-NMR (600 MHz, D$_2$O) δ: 4.06 (ddd, 1H, J$_{4,3a}$ 12.2, J$_{4,3b}$ 5.2, J$_{4,5}$ 3.1 Hz, H-4); 4.03 (ddd, 1H, J$_{6,7}$ 9.3, J$_{7,8b}$ 6.1, J$_{7,8a}$ 2.8 Hz, H-7); 4.02 (dd, 1H, J$_{4,5}$ 3.1, J$_{5,6}$ 0.8 Hz, H-5); 3.82 (dd, 1H, J$_{6,7}$ 9.3, J$_{5,6}$ 0.8 Hz, H-6); 3.60 (dd, 1H, J$_{8a,8b}$ 13.1, J$_{7,8a}$ 2.8 Hz, H-8a); 3.43 (dd, 1H, J$_{8a,8b}$ 13.1, J$_{7,8b}$ 6.1 Hz, H-8b); 1.98 (dd, 1H, J$_{3a,3b}$ 12.9, J$_{4,3a}$ 12.2 Hz, H-3a); 1.88 (dd, 1H, J$_{3a,3b}$ 12.9, J$_{4,3b}$ 5.2 Hz, H-3b).

$^{13}$C-NMR (150 MHz, D$_2$O) δ: 177.7 (C-1); 97.5 (C-2); 72.7 (C-6); 69.2 (C-7); 37.5 (C-5); 67.2 (C-4); 54.8 (C-8); 34.7 (C-3).

Major Conformer Alpha Furanose Form (NMR 5.5):

$^1$H-NMR (600 MHz, D$_2$O) δ: 4.50 (ddd, 1H, J$_{4,3a}$ 7.1, J$_{4,5}$ 3.5, J$_{4,3b}$ 3.2 Hz, H-4); 4.46 (dd, 1H, J$_{4,5}$ 3.5, J$_{5,6}$ 1.2 Hz, H-5); 3.85 (ddd, 1H, J$_{6,7}$ 9.0, J$_{7,8b}$ 5.9, J$_{7,8a}$ 2.7 Hz, H-7); 3.63 (dd, 1H, J$_{8a,8b}$ 13.2, J$_{7,8a}$ 2.7 Hz, H-8a); 3.63 (dd, 1H, J$_{6,7}$ 9.0, J$_{5,6}$ 1.2 Hz, H-6); 3.51 (dd, 1H, J$_{8a,8b}$ 13.2, J$_{7,8b}$ 5.9 Hz, H-8b); 2.59 (dd, 1H, J$_{3a,3b}$ 14.3, J$_{4,3a}$ 7.1 Hz, H-3a); 2.08 (dd, 1H, J$_{3a,3b}$ 14.3, J$_{4,3b}$ 3.2 Hz, H-3b).

$^{13}$C-NMR (150 MHz, D$_2$O) δ: 178.6 (C-1); 105.3 (C-2); 86.5 (C-5); 73.6 (C-4); 72.5 (C-6); 71.4 (C-7); 54.8 (C-8); 45.8 (C-3).

Minor Conformer Beta Furanose Form (NMR 2.5):

$^1$H-NMR (600 MHz, D$_2$O) δ: 4.52 (ddd, 1H, J$_{4,3b}$ 7.5, J$_{4,3a}$ 7.0, J$_{4,5}$ 6.0 Hz, H-4); 4.18 (dd, 1H, J$_{5,4}$ 6.0, J$_{5,6}$ 2.2 Hz, H-5); 3.86 (ddd, 1H, J$_{6,7}$ 8.9, J$_{7,8b}$ 6.1, J$_{7,8a}$ 2.4 Hz, H-7); 3.66 (dd, 1H, J$_{6,7}$ 8.9, J$_{5,6}$ 2.2 Hz, H-6); 3.64 (dd, 1H, J$_{8a,8b}$ 13.3, J$_{7,8a}$ 2.4 Hz, H-8a); 3.52 (dd, 1H, J$_{8a,8b}$ 13.3, J$_{7,8b}$ 6.1 Hz, H-8b); 2.37 (dd, 1H, J$_{3a,3b}$ 13.4, J$_{4,3a}$ 7.0 Hz, H-3a); 2.30 (dd, 1H, J$_{3a,3b}$ 13.4, J$_{4,3b}$ 7.5 Hz, H-3b).

$^{13}$C-NMR (150 MHz, D$_2$O) δ: 177.9 (C-1); 104.1 (C-2); 86.5 (C-5); 71.8 (C-4); 71.4 (C-7); 71.2 (C-6); 54.6 (C-8); 44.7 (C-3).

Minor Conformer Beta Pyranose Form (NMR 1.0):

$^1$H-NMR (600 MHz, D$_2$O) δ: 4.06-4.01 (m, 1H, H-4); 3.97 (ddd, 1H, J$_{6,7}$ 9.2, J$_{7,8b}$ 6.7, J$_{7,8a}$ 2.7 Hz, H-7); 3.96 (dd, 1H, J$_{4,5}$ 3.3, J$_{5,6}$ 1.1 Hz, H-5); 3.67 (dd, 1H, J$_{8a,8b}$ 13.2, J$_{7,8a}$ 2.7 Hz, H-8a); 3.53 (dd, 1H, J$_{6,7}$ 9.2, J$_{5,6}$ 1.1 Hz, H-6); 3.45 (dd, 1H, J$_{8a,8b}$ 13.2, J$_{7,8b}$ 6.7 Hz, H-8b); 2.33-2.27 (m, 1H, H-3a); 1.76 (dd, 1H, J$_{3a,3b}$ 12.6, J$_{4,3b}$ 12.1 Hz, H-3b).

$^{13}$C-NMR (150 MHz, D$_2$O) δ: 176.1 (C-1); 98.2 (C-2); 75.3 (C-6); 69.5 (C-7); 68.6 (C-4); 66.5 (C-5); 55.0 (C-8); 36.2 (C-3).

Invention Example 12

Use of ethyl (4S)-4-{(4R,5R)-5-[(R)-2-azido-1-hydroxyethyl]-2,2-dimethyl-1,3-dioxolan-4-yl}-4-hydroxy-2-oxobutanoate (9b) for the synthesis of ammonium 8-azido-3,8-dideoxy-D-gluco-oct-2-ulosonate (4eKdo-N$_3$) (10b)

Compound (10b)

To a solution of crude ethyl (4S)-4-{(4R,5R)-5-[(R)-2-azido-1-hydroxyethyl]-2,2-dimethyl-1,3-dioxolan-4-yl}-4-hydroxy-2-oxobutanoate (9b) (40 mg), as obtained from invention Example 10, in water (10 mL), trifluoroacetic acid (1 mL) was added and the mixture was stirred at 40° C. for 2 hours. Solvents were removed under reduced pressure without warming the bath and then co-evaporated twice with toluene to assure complete removal of acid. The residue was neutralized with ammonia (0.2 mol·L$^{-1}$) and then concentrated. Purification by flash column chromatography (ethyl acetate/ethanol/water 65:30:5) gave pure ammonium 8-azido-3,8-dideoxy-D-gluco-oct-2-ulosonate or 4eKdo-N$_3$ (10b) (24 mg, 46% starting from (8b)) as yellowish foam. Purity of more than 95% by NMR.

Rf (ethyl acetate/ethanol/water 65:30:5): 0.22.

IR (cm$^{-1}$): 3296, 2931, 2104, 1612, 1384, 1283, 1072, 805.

HRMS (ESI$^-$): [M-NH$_4$]$^-$ (C$_8$H$_{12}$N$_3$O$_7^-$) Calc. m/z: 262.0681, found: 262.0669.

Major Conformer Pyranose Form (NMR 7.5):

$^1$H-NMR (600 MHz, D$_2$O) δ: 4.15 (dd, 1H, J$_{6,7}$ 9.1, J$_{5,6}$ 1.0 Hz, H-6); 4.10 (ddd, 1H, J$_{4,5}$ 4.1, J$_{4,3a}$ 3.7, J$_{4,3b}$ 2.6 Hz, H-4); 4.03 (ddd, 1H, J$_{6,7}$ 9.1, J$_{7,8b}$ 6.3, J$_{7,8a}$ 2.8 Hz, H-7); 3.82 (dd, 1H, J$_{4,5}$ 4.1, J$_{5,6}$ 1.0 Hz, H-5); 3.63 (dd, 1H, J$_{8a,8b}$ 13.1, J$_{7,8a}$ 2.8 Hz, H-8a); 3.47 (dd, 1H, J$_{8a,8b}$ 13.1, J$_{7,8b}$ 6.3 Hz, H-8b); 2.23 (dd, 1H, J$_{3a,3b}$ 15.0, J$_{4,3a}$ 3.7 Hz, H-3a); 1.84 (dd, 1H, J$_{3a,3b}$ 15.0, J$_{4,3b}$ 2.6 Hz, H-3b).

$^{13}$C-NMR (150 MHz, D$_2$O) δ: 177.9 (C-1); 97.1 (C-2); 69.3 (C-7); 68.6 (C-6); 68.5 (C-4); 66.8 (C-5); 54.7 (C-8); 32.7 (C-3).

Major Conformer Furanose Form (NMR 3.0):

$^1$H-NMR (600 MHz, D$_2$O) δ: 4.61 (ddd, 1H, J$_{4,3b}$ 6.0, J$_{4,3a}$ 5.0, J$_{4,5}$ 4.8 Hz, H-4); 4.37 (dd, 1H, J$_{4,5}$ 4.8, J$_{5,6}$ 3.5 Hz, H-5); 3.91 (dd, 1H, J$_{6,7}$ 8.2, J$_{5,6}$ 3.5 Hz, H-6); 3.90 (ddd, 1H, J$_{6,7}$ 8.2, J$_{7,8b}$ 6.7, J$_{7,8a}$ 2.6 Hz, H-7); 3.59 (dd, 1H, J$_{8a,8b}$ 13.0, J$_{7,8a}$ 2.6 Hz, H-8a); 3.51 (dd, 1H, J$_{8a,8b}$ 13.0, J$_{7,8b}$ 6.7 Hz, H-8b); 2.40 (dd, 1H, J$_{3a,3b}$ 13.9, J$_{4,3a}$ 5.0 Hz, H-3a); 2.37 (dd, 1H, J$_{3a,3b}$ 13.9, J$_{4,3b}$ 6.0 Hz, H-3b).

$^{13}$C-NMR (150 MHz, D$_2$O) δ: 178.4 (C-1); 103.8 (C-2); 82.0 (C-5); 72.7 (C-4); 71.8, 71.6 (C-6, C-7); 54.1 (C-8); 45.6 (C-3).

Minor Conformer Pyranose Form (NMR 1.5):

$^1$H-NMR (600 MHz, D$_2$O) δ: 4.01 (ddd, 1H, J$_{4,5}$ 4.2, J$_{4,3a}$ 4.0, J$_{4,3b}$ 3.1 Hz, H-4); 3.96 (ddd, 1H, J$_{6,7}$ 8.9, J$_{7,8b}$ 6.2, J$_{7,8a}$ 2.7 Hz, H-7); 3.91 (dd, 1H, J$_{6,7}$ 8.9, J$_{5,6}$ 1.2 Hz, H-6); 3.76 (dd, 1H, J$_{4,5}$ 4.2, J$_{5,6}$ 1.2 Hz, H-5); 3.62 (dd, 1H, J$_{8a,8b}$ 13.2, J$_{7,8a}$ 2.7 Hz, H-8a); 3.45 (dd, 1H, J$_{8a,8b}$ 13.2, J$_{7,8b}$ 6.2 Hz, H-8b); 2.16 (dd, 1H, J$_{3a,3b}$ 15.1, J$_{4,3a}$ 4.0 Hz, H-3a); 2.12 (dd, 1H, J$_{3a,3b}$ 15.1, J$_{4,3b}$ 3.1 Hz, H-3b).

$^{13}$C-NMR (150 MHz, D$_2$O) δ: 176.7 (C-1); 96.8 (C-2); 69.4 (C-7); 70.9 (C-6); 68.5 (C-4); 66.9 (C-5); 54.8 (C-8); 34.2 (C-3).

Minor Conformer Furanose Form (NMR 1.0):

$^1$H-NMR (600 MHz, D$_2$O) δ: 4.58 (ddd, 1H, J$_{4,3a}$ 5.6, J$_{4,5}$ 4.1, J$_{4,3b}$ 1.7 Hz, H-4); 4.24 (dd, 1H, J$_{5,6}$ 4.5, J$_{4,5}$ 4.1 Hz, H-5); 3.97 (dd, 1H, J$_{6,7}$ 7.5, J$_{5,6}$ 4.5 Hz, H-6); 3.91 (ddd, 1H, J$_{6,7}$ 7.5, J$_{7,8b}$ 6.6, J$_{7,8a}$ 3.1 Hz, H-7); 3.60 (dd, 1H, J$_{8a,8b}$ 13.2, J$_{7,8a}$ 3.1 Hz, H-8a); 3.51 (dd, 1H, J$_{8a,8b}$ 13.2, J$_{7,8b}$ 6.6 Hz, H-8b); 2.55 (dd, 1H, J$_{3a,3b}$ 14.3, J$_{4,3a}$ 5.6 Hz, H-3a); 2.15 (dd, 1H, J$_{3a,3b}$ 14.3, J$_{4,3b}$ 1.7 Hz, H-3b).

$^{13}$C-NMR (150 MHz, D$_2$O) δ: 178.3 (C-1); 104.3 (C-2); 83.7 (C-5); 73.0 (C-4); 71.9 (C-6); 70.9 (C-7); 54.5 (C-8); 45.6 (C-3).

Invention Example 13

Use of Synthesis Intermediates (8a) or (8b) to Detect Gram Negative Bacteria

Material and Methods

1) Bacterial Strains and Growth Conditions.

Gram negative bacteria strains comprising *Legionella pneumophila* serogroup I, *Legionella gormanii* (*Fluoribacter gormanii*), *Escherichia coli* K12 and *Escherichia coli* O13 were grown in their specific culture medium. *Legionella pneumophila* serogroup 1 and *Legionella gormanii* (*Fluoribacter gormanii*) were grown in Yeast Extract medium supplemented with L-Cysteine, ferric pyrophosphate and α-ketoglutarate (YEC). *Escherichia coli* K12 and *Escherichia coli* O13 were grown in 2×YT medium (Yeast extract, tryptone and NaCl). All strains were grown in a rotary shaker (180 rpm) at 37° C.

2) Copper Catalyzed Click Chemistry Protocol.

Overnight cultures were diluted 100 times in fresh liquid medium with 1% of DMSO (final volume 300 μl) containing synthesis intermediates (8a) or (8b) (10 mM). Bacteria were incubated at 37° C. for 18 hours for *E. coli* strains and 24 hours for *Legionella* strains, and then aliquots of 200 μL were washed 2 times with PBS/DMSO (95:5) buffer (200 μL) and 1 time with PBS buffer (1X, 200 μL) by centrifugation at 12000×g for 1 min at room temperature.

The pellet was re-suspended in 200 μL of the "click" solution (CR110-CCH (0.10 mM), sodium ascorbate (5.0 mM), TGTA (4.0 mM) and copper sulfate pentahydrate (2.0 mM) in a mixture of PBS buffer and DMSO (99:1)) and transferred in a 2.0 mL microtube for a better agitation. This suspension was vigorously agitated in the dark for 30 min at room temperature, then the suspension was transferred back in a 1.5 mL microtube. Bacteria were washed 2 times with PBS/DMSO (95:5) buffer (200 μL) and 1 time with PBS buffer (200 μL, 12 000 rpm, 1 min, r.t.). The pellet was re-suspended in PBS buffer (200 μL) and kept at 4° C. in the dark. Bacteria were further analyzed by confocal microscopy.

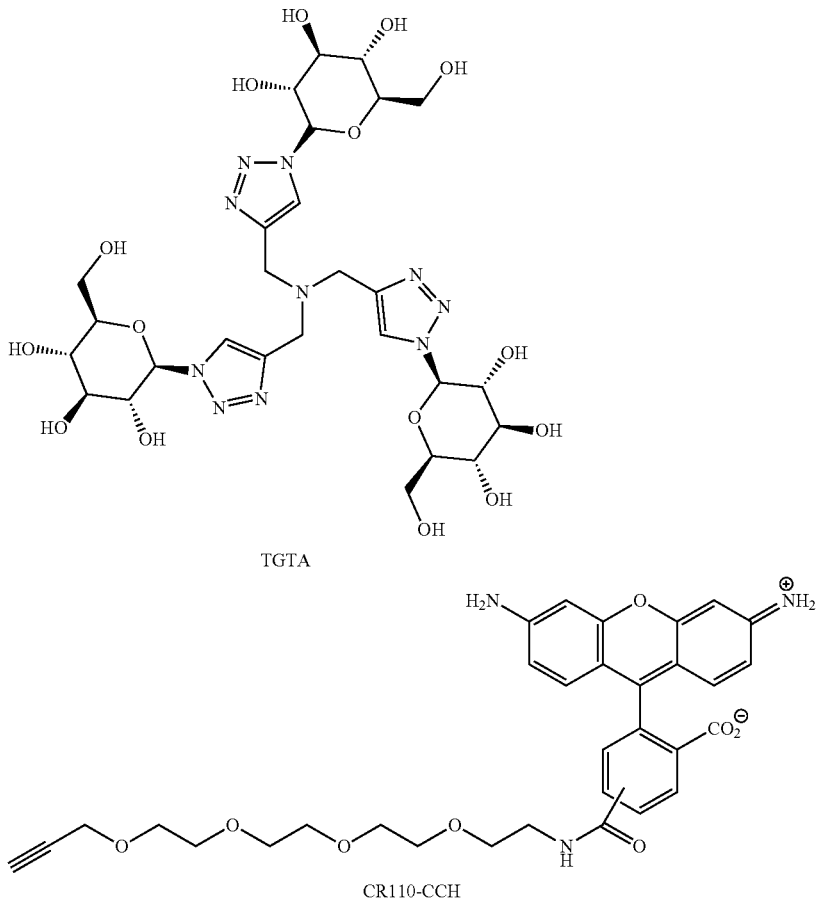

Results

Some of the Gram negative bacteria, including *E. coli* (K12 and O13), *Legionella* (*pneumophila* serogroup 1 and *gormanii*), were detected with synthesis intermediate compounds (8a) and (8b).

In conclusion, synthesis intermediate compounds (8a) and (8b) result in a clear labelling signal on the 4 examples of studied bacteria Gram negative.

SCHEME 1

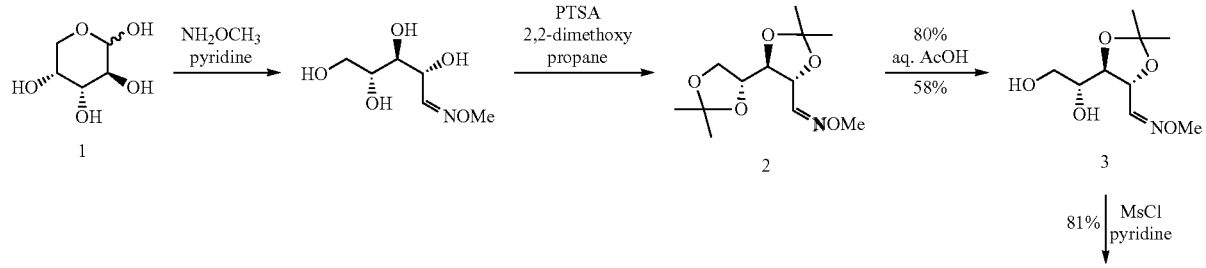

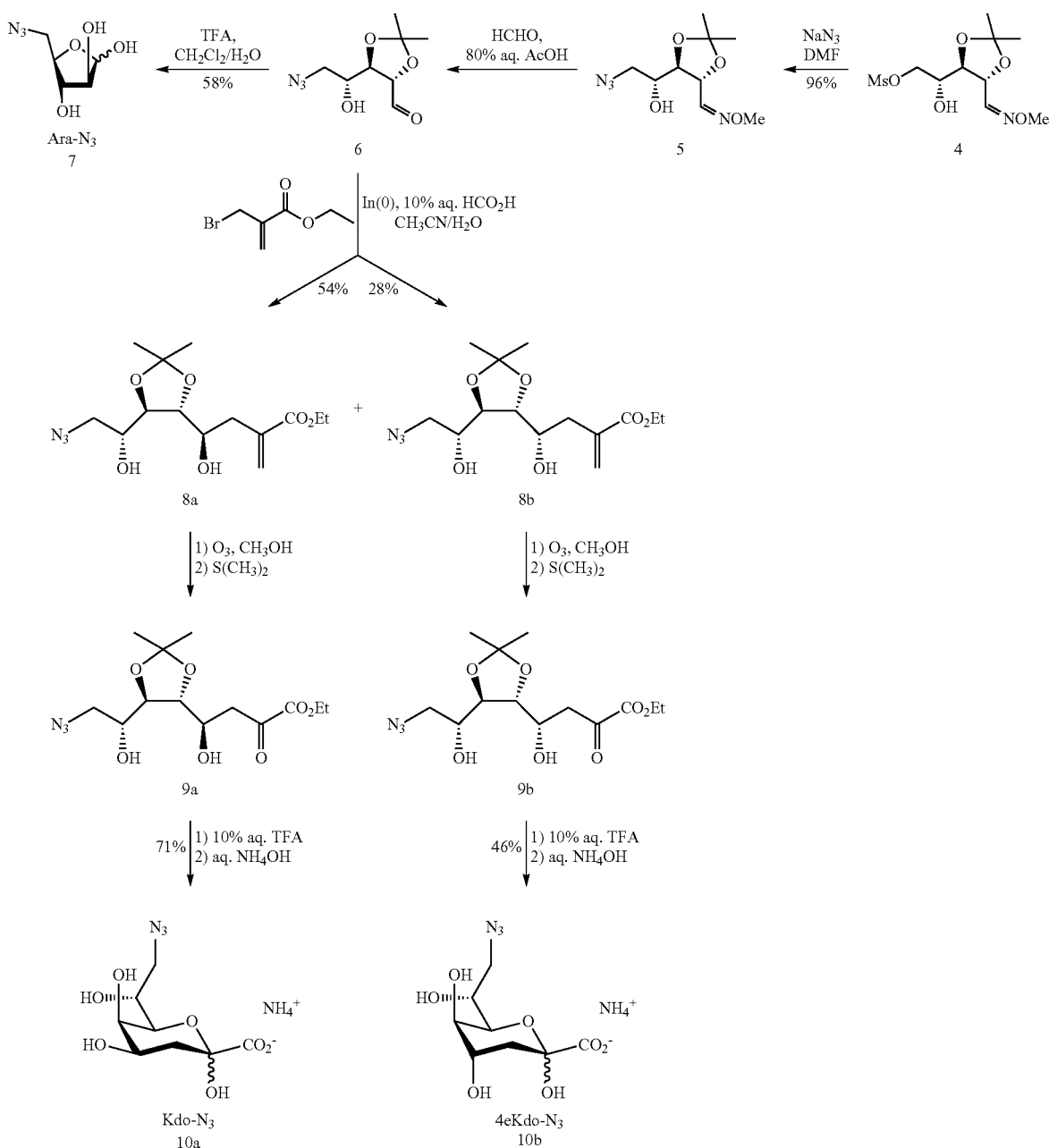

The synthesis starts from the commercially available D-arabinose and is providing an overall yield of 17 mol % for Kdo-N$_3$ with a purity of more than 95%, an overall yield of 6 mol % for 4eKdo-N$_3$ with a purity of more than 95% and an overall yield of 26 mol % for Ara-N$_3$ with a purity of more than 95%.

One skilled in the art will understand that various variations of the conditions of reaction of the invention can be made without departing from the core of the invention, including variations of the concentrations, nature of solvents, temperature, pressure, duration of reaction and stirring. Therefore, the invention covers all technical equivalents of the invention defined by the claims.

REFERENCES CITED

[1] Gao, J., Härter, R., Gordon, D. M., Whitesides, G. M., *J. Org. Chem.* 1994, 59, 3714-3715.

[2] Gillingham, D. G., Stallforth, P., Adibekian, A., Seeberger, P. H., Hilvert, D., *Nat. Chem.* 2010, 2, 102-105.

[3] Bird, J. W., Diaper, D. G. M., *Can. J. Chem.* 1969, 47, 145-150.

[4] Lee, J. G., Kwak, K. H., Hwang, J. P., *Tetrahedron Lett.* 1990, 31, 6677-6680.

[5] Chérest, M., Felkin, H., Prudent, N., *Tetrahedron Lett.* 1968, 18, 2199-2204; Anh, N. T., *Top. Curr. Chem.* 1980, 88, 145-162.

[6] Dumont, A., Malleron, A., Awwad, M., Dukan, S., Vauzeilles, B., *Angew. Chem. Int. Ed.* 2012, 51, 3143-3146.

[7] McNicholas, P. A., Batley, M., Redmond, J. W., *Carbohydrate Research*, 1987, 165, 17-22.

The invention claimed is:

1. A compound of formula V or VI, selected from:

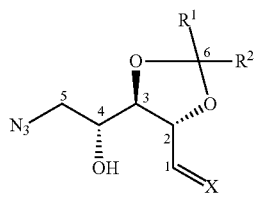

Formula V, X = NOR$^3$;
Formula VI, X = O wherein:
R$^1$ and R$^2$ are each independently H; a C$_1$ to C$_6$ alkyl; aryl; or R$^1$, R$^2$ together with the carbon C-6 are a cyclopentylidene or cyclohexylidene;
and R$^3$ is a C$_1$ to C$_6$ alkyl; or aryl.

2. A method of preparation of compound of formula VI according to claim 1 or 5-Azido-5-deoxy-2:3-isopropylidene-D-arabinose, comprising the chemical reaction of: either a compound of formula V:

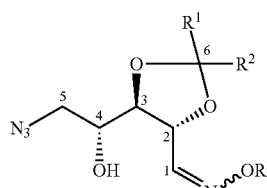

Formula (V)

wherein:
R$^1$ and R$^2$ are each independently H; a C$_1$ to C$_6$ alkyl; aryl; or R$^1$, R$^2$ together with the carbon C-6 are a cyclopentylidene or cyclohexylidene;
and R$^3$ is a C$_1$ to C$_6$ alkyl; or aryl;
or the specific compound (5), named 5-azido-5-deoxy-2:3-isopropylidene-D-arabinose O-methyloxime:

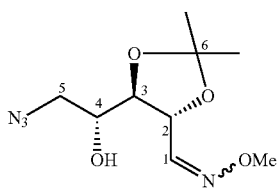

Compound (5)

with an aqueous solution of an organic or inorganic acid in the presence of an aldehyde.

3. A method of preparation of compound of formula V according to claim 1 or 5-azido-5-deoxy-2:3-isopropylidene-D-arabinose O-methyloxime, comprising the chemical reaction of: either a compound of formula IV:

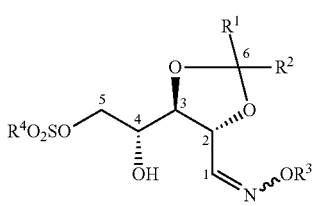

Formula (IV)

wherein:
R$^1$ and R$^2$ are each independently H; a C$_1$ to C$_6$ alkyl; aryl; or R$^1$, R$^2$ together with the carbon C-6 are a cyclopentylidene or cyclohexylidene;
and R$^3$ is a C$_1$ to C$_6$ alkyl; or aryl;
and R$^4$ is a C$_1$ to C$_6$ alkyl; a C$_1$ to C$_6$ perfluoroalkyl; or aryl;
or the specific compound (4), named 2:3-isopropylidene-5-O-methanesulfonyl-D-arabinose O-methyloxime:

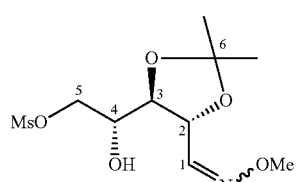

Compound (4)

with an organic or inorganic azide salt in a non-polar solvent or in polar aprotic solvent.

4. A method of preparation of compound of formula IV or of specific compound (4) according to claim 3, comprising the chemical reaction of: either a compound of formula III:

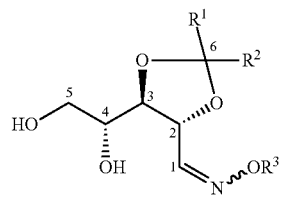

Formula (III)

wherein:
R$^1$ and R$^2$ can be are each independently H; a C$_1$ to C$_6$ alkyl; aryl; or R$^1$, R$^2$ together with the carbon C-6 are a cyclopentylidene or cyclohexylidene;
and R$^3$ is a C$_1$ to C$_6$ alkyl; or aryl;
or the specific compound (3), named 2:3-isopropylidene-D-arabinose O-methyloxime:

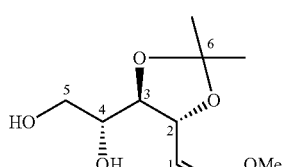

Compound (3)

with a sulfonyl chloride or sulfonic anhydride in the presence of an organic base and in the presence or not of a polar aprotic solvent.

5. A method for the synthesis of 5-azido-5-deoxy-D-arabinofuranose or Ara-N$_3$ (7):

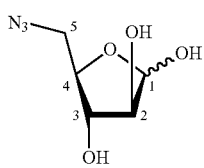

Compound (7)

comprising reacting synthesis intermediate of formula VI according to claim 1 or 5-Azido-5-deoxy-2:3-isopropylidene-D-arabinose, under reaction conditions providing removal of protecting group of compound of formula VI with an aqueous solution of an organic or inorganic acid in a polar aprotic solvent or non-polar solvent.

6. A method for the synthesis of:
either a compound of formula VIIIa:

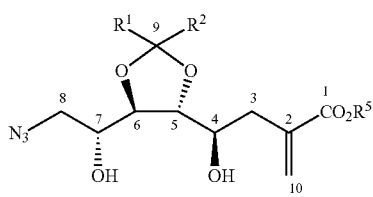

Formula (VIIIa)

wherein:
R$^1$ and R$^2$ are each independently H; a C$_1$ to C$_6$ alkyl; aryl; or R$^1$,R$^2$ together with the carbon C-6 are a cyclopentylidene or cyclohexylidene;
and R$^5$ is a C$_1$ to C$_6$ alkyl; or benzyl;
or the specific compound (8a), named ethyl (4R)-4-{(4R,5R)-5-[(R)-2-azido-1-hydroxyethyl]-2,2-dimethyl-1,3-dioxolan-4-yl)-4-hydroxy-2-methylenebutanoate:

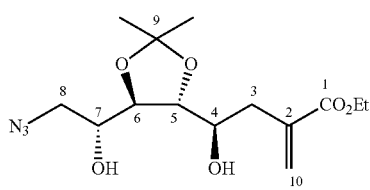

Compound (8a)

by reaction of compound of formula VI of claim 1 or 5 Azido-5-deoxy-2:3-isopropylidene-D-arabinose, with alkyl 2-(halomethyl)acrylate, in the presence of a metal, and the presence or not of an aqueous solution of an organic or inorganic acid, in a protic solvent or in a mixture of water and a polar aprotic solvent.

7. A method for the preparation of:
either a compound of formula IXa:

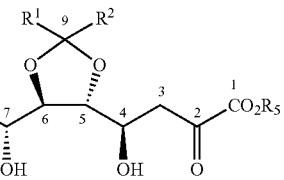

Formula (IXa)

wherein:
R$^1$ and R$^2$ are each independently H; a C$_1$ to C$_6$ alkyl; aryl; or R$^1$,R$^2$ together with the carbon C-6 are a cyclopentylidene or cyclohexylidene;
and R$^5$ is a C$_1$ to C$_6$ alkyl; or benzyl;
or the specific compound (9a), named (4R)-4-{(4R,5R)-5-[(R)-2-azido-1-hydroxyethyl]-2,2-dimethyl-1,3-dioxolan-4-yl)-4-hydroxy-2-oxobutanoate:

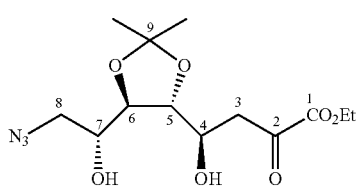

Compound (9a)

comprising performing an ozonolysis of compound of formula VIIIa or of specific compound (8a) according to claim 6, with ozone in a protic solvent, at a temperature between −100 and 0° C., and then the unstable intermediate compound being reacted with a reducing agent, in a protic solvent.

8. A method for the preparation of ammonium 8-azido-3,8-dideoxy-D-manno-oct-2-ulosonate or Kdo-N$_3$ (10a):

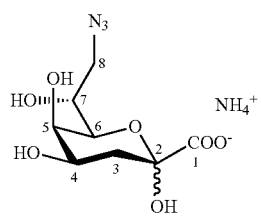

Compound (10a)

comprising deprotecting compound of formula IXa or specific compound (9a) according to claim 7, with an aqueous solution of an organic or inorganic acid.

9. A method for the synthesis of:
either a compound of formula VIIIb:

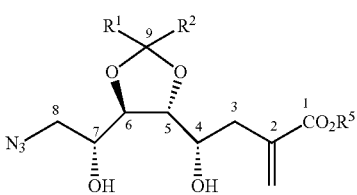

Formula (VIIIb)

wherein:

$R^1$ and $R^2$ can be are each independently H; a $C_1$ to $C_6$ alkyl; aryl; or $R^1, R^2$ together with the carbon C-6 are a cyclopentylidene or cyclohexylidene;

and $R^5$ is a $C_1$ to $C_6$ alkyl; or benzyl;

or the specific compound (8b), named ethyl (4S)-4-{(4R, 5R)-5-[(R)-2-azido-1-hydroxyethyl]-2,2-dimethyl-1,3-dioxolan-4-yl)-4-hydroxy-2-methylenebutanoate:

Compound (8b)

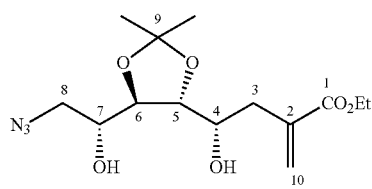

by reaction of compound of formula VI or 5-Azido-5-deoxy-2:3-isopropylidene-D-arabinose according to claim 1 with alkyl 2-(halomethyl)acrylate, in the presence of a metal, and the presence or not of an aqueous solution of an organic or inorganic acid, in a protic solvent or in a mixture of water and a polar aprotic solvent.

10. A method for the preparation of:
either a compound of formula IXb:

Formula (IXb)

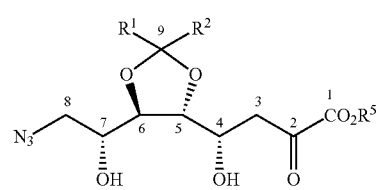

wherein:

$R^1$ and $R^2$ are each independently H; a $C_1$ to $C_6$ alkyl; aryl; or $R^1, R^2$ together with the carbon C-6 are a cyclopentylidene or cyclohexylidene;

and $R^5$ is a $C_1$ to $C_6$ alkyl; or benzyl;

or the specific compound (9b), named (4S)-4-{(4R,5R)-5-[(R)-2-azido-1-hydroxyethyl]-2,2-dimethyl-1,3-dioxolan-4-yl)-4-hydroxy-2-oxobutanoate:

Compound (9b)

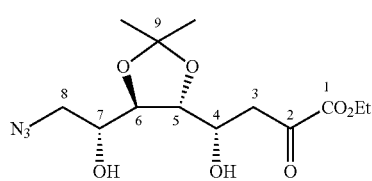

comprising performing an ozonolysis of compound of formula VIIIb or of specific compound (8b) of claim 9, with ozone in a protic solvent, at a temperature between −100 and 0° C., and then the unstable intermediate compound being reacted with a reducing agent, in a protic solvent.

11. A method for the preparation of ammonium 8-azido-3,8-dideoxy-D-gluco-oct-2-ulosonate or 4eKdo-N3 (10b):

Compound (10b)

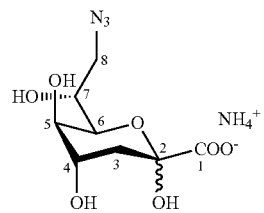

comprising deprotecting compound of formula IXb or specific compound (9b) of claim 10, with an aqueous solution of an organic or inorganic acid.

12. A compound selected from the group consisting of:
a)

Formula (IXa)

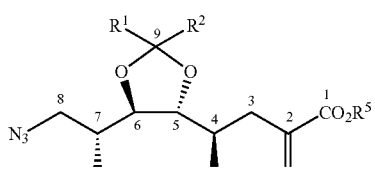

wherein:

$R^1$ and $R^2$ are each independently H; a $C_1$ to $C_6$ alkyl; aryl; or $R^1$, $R^2$ together with the carbon C-6 are a cyclopentylidene or cyclohexylidene;

and $R^5$ is a C to $C_6$ alkyl; or benzyl; and b)

Formula (VIIIa)

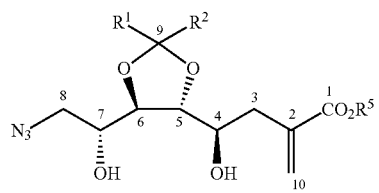

wherein:

$R^1$ and $R^2$ are each independently H; a $C_1$ to $C_6$ alkyl; aryl; or $R^1$, $R^2$ together with the carbon C-6 are a cyclopentylidene or cyclohexylidene;

and $R^5$ is a $C_1$ to $C_6$ alkyl; or benzyl; and c)

Formula (IXb)

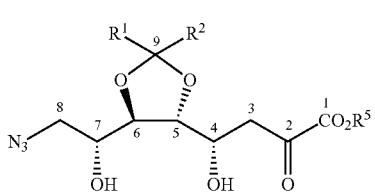

wherein:

$R^1$ and $R^2$ are each independently H; a $C_1$ to $C_6$ alkyl; aryl; or $R^1$, $R^2$ together with the carbon C-6 are a cyclopentylidene or cyclohexylidene;

and $R^5$ is a C to $C_6$ alkyl; or benzyl; and d)

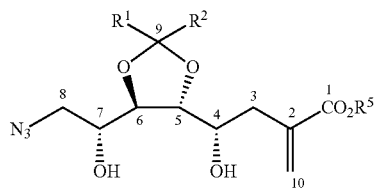

Formula (VIIIb)

wherein:
R¹ and R² are each independently H; a $C_1$ to $C_6$ alkyl; aryl; or R¹, R² together with the carbon C-6 are a cyclopentylidene or cyclohexylidene;
and R⁵ is a $C_1$ to $C_6$ alkyl; or benzyl; and e)

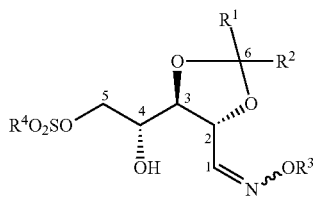

Formula (IV)

wherein:
R¹ and R² are each independently H; a $C_1$ to $C_6$ alkyl; aryl; or R¹, R² together with the carbon C-6 are a cyclopentylidene or cyclohexylidene;
and R³ is a $C_1$ to $C_6$ alkyl; or aryl;
and R⁴ is a $C_1$ to $C_6$ alkyl; a $C_1$ to $C_6$ perfluoroalkyl; or aryl.

13. Method for the detection of bacteria, comprising contacting a compound of formula VIIIa or VIIIb, according to claim 12, with a culture medium comprising the bacteria.

14. A method of preparation of compound of formula V or of specific compound (5) according to claim 1, comprising the chemical reaction of:
either a compound of formula IV:

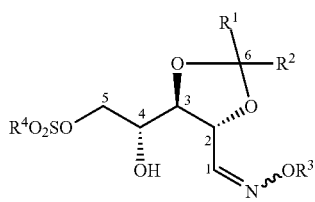

Formula (IV)

wherein:
R¹ and R² are each independently H; a $C_1$ to $C_6$ alkyl; aryl; or R¹, R² together with the carbon C-6 are a cyclopentylidene or cyclohexylidene;

and R³ is a $C_1$ to $C_6$ alkyl; or aryl;
and R⁴ is a $C_1$ to $C_6$ alkyl; a $C_1$ to $C_6$ perfluoroalkyl; or aryl;
or the specific compound (4), named 2:3-isopropylidene-5-O-methanesulfonyl-D-arabinose O-methyloxime:

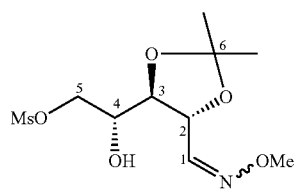

Compound (4)

with an organic or inorganic azide salt in a non-polar solvent or in polar aprotic solvent.

15. A method of preparation of compound of formula IV or of specific compound (4) according to claim 14, comprising the chemical reaction of:
either a compound of formula III:

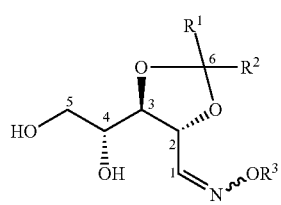

Formula (III)

wherein:
R¹ and R² are each independently H; a $C_1$ to $C_6$ alkyl; aryl; or R¹, R² together with the carbon C-6 are a cyclopentylidene or cyclohexylidene;
and R³ is a $C_1$ to $C_6$ alkyl; or aryl;
or the specific compound (3), named 2:3-isopropylidene-D-arabinose O-methyloxime:

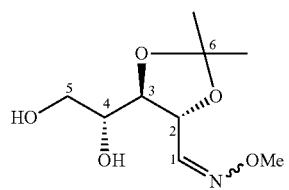

Compound (3)

with a sulfonyl chloride or sulfonic anhydride in the presence of an organic base and in the presence or not of a polar aprotic solvent.

* * * * *